(12) United States Patent
Deng et al.

(10) Patent No.: US 10,676,713 B2
(45) Date of Patent: Jun. 9, 2020

(54) BIOACTIVE BOROPHOSPHATE GLASSES

(71) Applicant: Corning Incorporated, Corning, NY (US)

(72) Inventors: Huayun Deng, Painted Post, NY (US); Ye Fang, Painted Post, NY (US); Qiang Fu, Painted Post, NY (US); Aize Li, Painted Post, NY (US); Lina Ma, Corning, NY (US); John Christopher Mauro, Corning, NY (US)

(73) Assignee: Corning Incorporated, Corning, NY (US)

( * ) Notice: Subject to any disclaimer, the term of this patent is extended or adjusted under 35 U.S.C. 154(b) by 0 days.

(21) Appl. No.: 15/602,899

(22) Filed: May 23, 2017

(65) Prior Publication Data
US 2017/0349876 A1    Dec. 7, 2017

Related U.S. Application Data

(60) Provisional application No. 62/342,426, filed on May 27, 2016.

(51) Int. Cl.
| | |
|---|---|
| *C12N 5/00* | (2006.01) |
| *C03C 3/145* | (2006.01) |
| *C03C 4/00* | (2006.01) |
| *C03C 3/16* | (2006.01) |
| *C03C 3/21* | (2006.01) |
| *C03C 3/062* | (2006.01) |
| *C03C 3/17* | (2006.01) |
| *C03C 3/064* | (2006.01) |
| *C03C 3/19* | (2006.01) |
| *C12N 5/071* | (2010.01) |

(52) U.S. Cl.
CPC ............ *C12N 5/0068* (2013.01); *C03C 3/062* (2013.01); *C03C 3/064* (2013.01); *C03C 3/145* (2013.01); *C03C 3/16* (2013.01); *C03C 3/17* (2013.01); *C03C 3/19* (2013.01); *C03C 3/21* (2013.01); *C03C 4/0007* (2013.01); *C03C 4/0014* (2013.01); *C03C 4/0035* (2013.01); *C12N 5/069* (2013.01); *C12N 2500/30* (2013.01); *C12N 2501/105* (2013.01); *C12N 2501/11* (2013.01); *C12N 2501/115* (2013.01); *C12N 2501/165* (2013.01); *C12N 2501/30* (2013.01); *C12N 2501/91* (2013.01); *C12N 2533/12* (2013.01)

(58) Field of Classification Search
CPC .. C03C 6/62; C03C 3/64; C03C 3/145; C03C 3/16; C03C 3/17; C03C 3/19; C03C 3/21; C03C 4/0007; C03C 4/0014; C03C 4/0035; C12N 2500/30; C12N 2501/105; C12N 2501/11; C12N 2501/115; C12N 2501/2501; C12N 2501/165; C12N 2501/30; C12N 2501/91; C12N 2501/12; C12N 5/0068; C12N 5/069
See application file for complete search history.

(56) References Cited

U.S. PATENT DOCUMENTS

| | | |
|---|---|---|
| 2,532,386 A | 12/1950 | Armistead |
| 2,978,339 A | 4/1961 | Veatch et al. |
| 3,323,888 A | 6/1967 | Searight et al. |
| 3,778,335 A | 12/1973 | Boyd |
| 3,790,430 A | 2/1974 | Mochel |
| 4,083,727 A | 4/1978 | Andrus et al. |
| 4,084,972 A | 4/1978 | Andrus et al. |
| 4,126,437 A | 11/1978 | O Horo |
| 4,140,645 A | 2/1979 | Beall et al. |
| 4,233,169 A | 11/1980 | Beall et al. |
| 4,323,056 A | 4/1982 | Borrelli et al. |
| 4,340,693 A | 7/1982 | Drake |
| 4,889,707 A | 12/1989 | Day |
| 5,081,394 A | 1/1992 | Morishita et al. |
| 5,153,070 A | 10/1992 | Andrus |

(Continued)

FOREIGN PATENT DOCUMENTS

| | | |
|---|---|---|
| CA | 2577628 C | 11/2010 |
| CA | 2926665 A1 | 5/2015 |

(Continued)

OTHER PUBLICATIONS

Abo-Naf et al. Spectrochimica Acta Part A: Molec. Spectroscopy (2015; available online Feb. 26, 2015) 144: 88-98 (Year: 2015).*
Sharmin et al. BioMed Research Int. (2013) vol. 2013, Article ID 902427, pp. 1-12 (Year: 2013).*
Ohgushi et al. Bioceramics vol. 11, LeGeros et al, Ed., Proc. 11th Int. Symp. Ceramics Med. (NY: NY), Nov. 1998, pp. 261-264 (Year: 1998).*
Buchilin et al. J. Non-Crystalline Solids (2013) 373-374: 42-40 (Year: 2013).*
Zheng et al. J. Non-Crystalline Solids (2012) 358: 387-391 (Year: 2012).*
Franks et al. J. Materials Sci.: Materials in Medicine (2002) 13: 459-536 (Year: 2002).*
Gorustovich et al. (J. Biomed. Materials Res., Prat A (2010) 92A: 232-237 (Year: 2010).*
L. Hench et al., "Third-Generation Biomedical Materials", Science, vol. 295, Feb. 8, 2002, p. 1016-1017, www.sciencemag.org, Downloaded from www.sciencemag.org on Aug. 5, 2015.

(Continued)

*Primary Examiner* — Susan M Hanley

(57) ABSTRACT

A borophosphate glass composition including $B_2O_3$, $P_2O_5$, and CaO, and optionally a source additive selected from: $Li_2O$, $Na_2O$, $K_2O$, $Al_2O_3$, ZnO, MgO, $Fe_2O_3$/FeO, CuO/$Cu_2O$, and mixtures thereof, as defined herein. Also disclosed are bioactive compositions or substrates including the disclosed borophosphate glass composition, and at least one live cell. Also disclosed are methods of inhibiting or increasing the relative amount of species containing boron, phosphorous, or both, being released into an aqueous solution from aborophosphate glass composition defined herein. Also disclosed is a method of proliferating cells on a bioactive substrate as defined herein. Also disclosed are related glass compositions that exclude one of $B_2O_3$, $P_2O_5$, and CaO.

19 Claims, 12 Drawing Sheets

(56) References Cited

U.S. PATENT DOCUMENTS

| | | |
|---|---|---|
| 5,648,124 A | 7/1997 | Sutor |
| 5,674,790 A | 10/1997 | Araujo |
| 5,849,816 A | 12/1998 | Suskind et al. |
| 5,876,452 A | 3/1999 | Athanasiou et al. |
| 6,214,471 B1 | 4/2001 | Beall |
| 6,254,981 B1 | 7/2001 | Castle |
| 6,280,863 B1 | 8/2001 | Frank et al. |
| 6,328,990 B1 | 12/2001 | Ducheyne et al. |
| 6,338,751 B1 | 1/2002 | Litkowski et al. |
| 6,506,399 B2 | 1/2003 | Donovan |
| 6,514,892 B1 | 2/2003 | Kasai et al. |
| 6,802,894 B2 | 10/2004 | Brodkin |
| 6,838,171 B2 | 1/2005 | Nomura |
| 6,852,656 B1 | 2/2005 | La Greca et al. |
| 7,166,548 B2 | 1/2007 | Apel et al. |
| 7,166,549 B2 | 1/2007 | Fechner et al. |
| 7,597,900 B2 | 10/2009 | Zimmer et al. |
| 7,704,903 B2 | 4/2010 | Seneschal et al. |
| 7,709,027 B2 | 5/2010 | Fechner et al. |
| 7,905,115 B2 | 3/2011 | Rake et al. |
| 7,989,065 B2 | 8/2011 | Winstead |
| 8,080,490 B2 | 12/2011 | Fechner et al. |
| 8,173,154 B2 | 5/2012 | Jung et al. |
| 8,637,300 B2 | 1/2014 | Ruf et al. |
| 9,056,045 B2 | 6/2015 | Hughes |
| 9,084,844 B2 | 7/2015 | Vallittu |
| 9,168,272 B2 | 10/2015 | Hill et al. |
| 9,326,995 B2 | 5/2016 | Stucky et al. |
| 9,498,459 B2 | 11/2016 | Pomrink et al. |
| 9,622,483 B2 | 4/2017 | Bookbinder et al. |
| 9,688,567 B2 | 6/2017 | Rampf et al. |
| 9,701,573 B2 | 7/2017 | Beall et al. |
| 2004/0120908 A1 | 6/2004 | Cohen et al. |
| 2004/0228905 A1 | 11/2004 | Greenspan et al. |
| 2005/0118236 A1 | 6/2005 | Qiu et al. |
| 2005/0142077 A1 | 6/2005 | Zimmer et al. |
| 2005/0158395 A1 | 7/2005 | Zimmermann et al. |
| 2006/0127427 A1 | 6/2006 | Vernice et al. |
| 2007/0122356 A1 | 5/2007 | Kessler et al. |
| 2008/0214428 A1 | 9/2008 | Orlich et al. |
| 2008/0233201 A1 | 9/2008 | Royere |
| 2009/0208428 A1 | 8/2009 | Hill |
| 2011/0009254 A1 | 1/2011 | Schweiger et al. |
| 2011/0152057 A1 | 6/2011 | Qi |
| 2012/0020898 A1 | 1/2012 | Mandadi et al. |
| 2012/0135848 A1 | 5/2012 | Beall et al. |
| 2012/0317735 A1 | 12/2012 | Gonzales |
| 2012/0321567 A1 | 12/2012 | Gonzales |
| 2013/0266625 A1 | 10/2013 | Benita |
| 2014/0026916 A1 | 1/2014 | Havens |
| 2014/0186274 A1 | 7/2014 | Hodgkinson |
| 2014/0193499 A1 | 7/2014 | Da Fonte Ferreira |
| 2014/0212469 A1 | 7/2014 | Rahaman |
| 2014/0271913 A1 | 9/2014 | Pomrink et al. |
| 2014/0349831 A1 | 11/2014 | Cornejo et al. |
| 2014/0370464 A1 | 12/2014 | Kounga et al. |
| 2015/0087493 A1 | 3/2015 | Ritzberger |
| 2015/0231042 A1 | 8/2015 | Gonzales |
| 2015/0239772 A1 | 8/2015 | Baker |
| 2015/0265509 A1 | 9/2015 | Zhang et al. |
| 2015/0299031 A1 | 10/2015 | Ritzberger et al. |
| 2015/0374589 A1 | 12/2015 | Rampf et al. |
| 2016/0102010 A1 | 4/2016 | Beall et al. |
| 2016/0145567 A1 | 5/2016 | Henry et al. |
| 2017/0086877 A1 | 3/2017 | Moffarah et al. |
| 2017/0274118 A1 | 9/2017 | Nazhat et al. |
| 2017/0340527 A1 | 11/2017 | Chang et al. |
| 2017/0340666 A1 | 11/2017 | Deng et al. |
| 2017/0341975 A1 | 11/2017 | Gross et al. |
| 2017/0342382 A1 | 11/2017 | Deng et al. |
| 2017/0342383 A1 | 11/2017 | Deng et al. |
| 2017/0349876 A1 | 12/2017 | Deng et al. |
| 2017/0354755 A1 | 12/2017 | Weinberger et al. |
| 2018/0343255 A1 | 11/2018 | Thibadeau, Sr. et al. |
| 2019/0060523 A1 | 2/2019 | Bakry |

FOREIGN PATENT DOCUMENTS

| | | | |
|---|---|---|---|
| EP | 935526 A1 | 8/1999 | |
| EP | 1452496 A1 | 9/2004 | |
| EP | 1021148 B1 | 5/2008 | |
| HU | 227595 B1 | 9/2011 | |
| JP | 2004359754 A | 12/2004 | |
| JP | 2007001846 A | 1/2007 | |
| JP | 2007039269 A | 2/2007 | |
| KR | 200781952 | 8/2007 | |
| WO | 199962835 A1 | 12/1999 | |
| WO | WO-9962835 A1 * | 12/1999 | ............... C03C 3/16 |
| WO | 2007141978 A1 | 12/2007 | |
| WO | 2008000888 A2 | 1/2008 | |
| WO | 2011141896 A1 | 11/2011 | |
| WO | 2012137158 | 10/2012 | |
| WO | 2014095198 A1 | 6/2014 | |
| WO | 2014159240 A1 | 10/2014 | |
| WO | 2015034860 | 3/2015 | |
| WO | 2015123049 A1 | 8/2015 | |
| WO | 2015200017 A1 | 12/2015 | |

OTHER PUBLICATIONS

L.L.Hench, "Bioceramics", J. Am. Ceram. Soc., 81, (7), 1705-1728 (1998).
T. Kokubo et al., "How useful is SBF in predicting in vivo bone bioactivity?", Biomaterials, 27, (2006), 2907-2915.
Qiang Fu et al., "Bioactive glass scaffolds for bone tissue engineering: state of the art and future perspectives", Materials Science and Engineering, C 31, (2011), 1245-1256.
L. Peddi et al., "Bioactive borate glass coatings for titanium alloys", J. Mater. Sci: Mater. Med., (2008), 19, p. 3145-3152.
Mohamed N. Rahaman et al., "Bioactive glass in tissue engineering", Acta Biomaterialia, 7, (2011), 2355-2373.
WO2012137158 machine translation.
Dutra Zanotto, "A bright future for glass-ceramics", American Ceramic Society Bulletin, vol. 89, No. 8, pp. 19-27, 2010
American Type Culture Collection, Product Sheet MC3T3E1, Subclone 14, (ATCC® CRL2594™), p. 1-3, Aug. 2014.
Maziar Montazerian, et al. "History and trends of bioactive glass-ceramics", Journal of Biomedical Materials Research A, 2016, vol. 104A, 1231-1249, 2016 Wiley Periodicals, Inc.
Apel et al., "Influence of ZrO2 on the crystallization and properties of lithium disilicate glass-ceramics derived from a multi-component system", J Eur Ceram Soc, 2007, 27:1571-1577.
Antonio Tilocca et al., "Structural Effects of Phosphorus Inclusion in Bioactive Silicate Glasses", J. Phys. Chem. B 2007, 111, 14256-14264.
K. Franks et al., "The effect of MgO on the solubility behaviour and cell proliferation in a quaternary soluble phosphate baed glass system", J. of Mate. Sciemce: Materials in Medicine, 13, (2002), 549-556.
I. Ahmed et al., "Processing, characterisation and biocompatibility of iron-phosphate glass fibres for tissue engineering", Biomaterials, 25, (2004), 3223-3232.
Huipin Yuan, et al., "Osteoinduction by calciumphosphate biomaterials", Journal of Materials Science: Materials in Medicine 9 (1998) 723-726.
Jianxi Lu, et al., The Biodegradation Mechanism of Calcium Phosphate Biomaterials in Bone, Journal of Biomedical Materials Research, Aug. 2002, 63(4): 408-412.
B.C. Bunker, et al., Phosphate Glass Dissolution in Aqueous Solutions, Journal of Non-Crystalline Solids 64 (1984) 291-316.
Jonathan C. Knowles, Phosphate based glasses for biomedical applications, J. Mater. Chem., 2003, 13, 2395-2401.
Motohiro Uo et al., Properties and cytotoxicity of water soluble Na2O—CaO—P2O5 glasses, Biomaterials, 19, (1998), 2277-2284.
F. Jay Murray, Issues in Boron Risk Assessment: Pivotal Study, Uncertainty Factors, and ADIs, The Journal of Trace Elements in Experimental Medicine 9, No. 4 (1996): 231-243.
R.F. Brown, et al., "Effect of borate glass composition on its conversion to hydroxyapatite and on the proliferation of MC3T3-E1 cells." Journal of Biomedical Materials Research Part A, 88, No. 2, (2009): 392-400.

(56) References Cited

OTHER PUBLICATIONS

A. Saranti, et al., "Bioactive glasses in the system CaO—B2O3—P2O5: preparation, structural study and in vitro evaluation." Journal of Non-Crystalline Solids 352, No. 5 (2006): 390-398.
L. Hench, and J. Jones, eds. Biomaterials, artificial organs and tissue engineering. Elsevier, 2005—book.
E.A. Abou Neel,et al., "Effect of iron on the surface, degradation and ion release properties of phosphate-based glass fibres." Acta Biomaterialia 1, No. 5 (2005): 553-563.
E.A. Abou Neel, et al., "Characterisation of antibacterial copper releasing degradable phosphate glass fibres.", Biomaterials 26, No. 15 (2005): 2247-2254.
C. M. Rochman,et al., Scientific evidence supports a ban on microbeads, Environ Sci & Tech, 2015, 49: 10759-10761.
Wei Xiao et al., "Hollow hydroxyapatite microspheres: a novel bioactive and osteoconductive carrier for controlled release of bone morphogenetic protein-2 in bone regeneration", Acta Biomater. Sep. 2013; 9(9): 8374-8383.
Wanpeng Cao et al., Bioactive Materials, Ceramics International, 22, (1996) 493-507.
Fabienne C. Raszewski et al., Methods for Producing Hollow Glass Microspheres, Savannah River National Laboratory, Aiken, SC 29808, Mar. 2016.
Imogen E. Napper et al., Characterisation, quantity and sorptive properties of microplastics extracted from cosmetics, Marine Pollution Bulletin, vol. 99, Issues 1-2, Oct. 15, 2015, pp. 178-185.
Alexis J. de Kerchove et al., Formation of Polysaccharide Gel Layers in the Presence of Ca2+ and K+ Ions: Measurements and Mechanisms, Biomacromolecules, Aug. 2007, 113-121.
Marianne Hiorth et al., Immersion coating of pellets with calcium pectinate and chitosan, International Journal of Pharmaceutics 308 (2006) 25-32.
Fuat Topuz, et al., Magnesium ions and alginate do form hydrogels: a rheological study, Soft Matter, Aug. 2012, 4877-4881.
Yrr A. Mørch, et al., Effect of Ca2+, Ba2+, and Sr2+ on Alginate Microbeads, Biomacromolecules Jul. 2006, 1471-1480.
Bertling, et al., "Hollow microspheres." Chem Eng Technol, 2004, 27: 829-837.
International Searching Authority Invitation to Pay Additional Fees and Partial Search Report PCT/US2017034417 dated Oct. 27, 2017.
V. V. Budov, Hollow glass microspheres. Use, properties and technology (review article), Glass Ceram, 1994, 51: 230-235.
International Search Report and Written Opinion PCT/US2017/034417 dated Jan. 9, 2018.
C.D.Graham, "High-Sensitivity Manetization Measurements", J. Mater. Sci. Technol., 2000, 16(2): 97-101.
Fu, H., et al., Hollow hydroxyapatite microspheres as a device for controlled delivery of proteins. J Mater Sci: Mater Med., 2011, 22: 579-91.
Huang, et al., "Kinetics and mechanisms of the conversion of silicate (45S5), borate and borosilicate glasses to hydroxyapatite in dilute phosphate solutions," J Mater Sci Mater Med 2006, 17: 583-596.
Fu et al; "Silicate, Borosilicate, and Borate Bioactive Glass Scaffolds With Controllable Degradation Rate for Bone Tissue Engineering Applications. I. Prepareation and in Vitro Degradation"; Journal of Biomedical Materials Research A; 2010; vol. 95A; Issue 1; pp. 164-171.
Holand et al; "A Comparison of the Microstructure and Properties of the IPS EMPRESST2 and the IPS EMPRESST Glass-Ceramics"; J Biomed Mater Res (Appl Biomater), 2000, 53: 297303.
"An In-Vitro Comparison of Nano Hydroxyapatite, Novamin and Proargin Desensitizing Toothpastes—A SEM Study"; J Clin Diagn Res, 2016, 10(10): ZC51ZC54.
Cao Et La; "Methods for Biomimetic Remineralization of Human Dentine: A Systematic Review"; Int. J. Mol. Sci. (2015) 16; pp. 4615-4627.
Copeland et al; "Microbeads: An Emerging Water Quality Issue", Retrieved From fas.org, Jul. 20, 2015, 2 Pgs.
Coradin et al; "Silica-Alginate Composites for Microencapsulation" Applied Microbiology and Biotechnology, 61(5-6) pp. 429-434 (2003).
Davari, "Dentin Hypersensitivity: Etiology, Diagnosis and Treatment, A Literature Review," J Dent (Shiraz), 2013, 14(3): 136145).
Dentinal Hypersensitivity: Etiology, Diagnosis and Management "; 9 Pages; Date Unknown; www.indeedce.com".
El-Kheshen et al. Ceramics Int. (2008) 34: 1667-1673 (Year: 2008).
Fendall et al; "Contributing to Marine Pollution by Washing Your Face: Microplasitcs in Facial Cleansers"; Marine Pollution Bulletin 58 (8): 12251228 (2009.
Forsback et al; "Mineralization of Dentin Induced by Treatment With Bioactive Glass S53P4 in Vitro"; Acta Odontol Scand, 62 (2004); pp. 14-20.
Fu et al; "Bioactive Glass Innovations Through Academia-Industry Collaboration"; International Journal of Applied Glass Science, 7 [2], (2016) pp. 139-146.
Fu et al; "Nature-Inspired Design of Strong, Tough Glass-Ceramics," MRS Bulletin, 2017, 42:220-225.
Gy, "Ion Exchange for Glass Strengthening," Mater Sci EHG B, 2008, 149: 159-165.
Han et al; "In Vivo Remineralization of Dentin Using an Agarose Hydrogel Biomimetic Mineralization System"; Nature, Scientific Reports; (2017); 9 Pages.
Jacoby; "New Applications for Glass Emerge," Chem. Eng. News, 90 [25] 3436 (2012).
Jones; "Review of Bioactive Glass: From Hench to Hybrids"; Acta Biomaterialia 9 (2013) pp. 4457-4486.
Kulal et al; "An In-Vitro Comparison of Nano Hydroxyapatite, Novamin and Proargin Desensitizing Toothpastes—A SEM Study"; Journal of Clinical and Diagnostic Research; 2016; vol. 10 (10) ZC51-ZC54.
Kumaryadav et al; "Development of Zirconia Substituted 1393 Bioactive Glass for Orthopaedic Application"; Oriental Journal of Chemistry; vol. 33, No. 6; (2017) pp. 2720-2730.
Lien et al; "Microstructural Evolution and Physical Behavior of a Lithium Disilicate Glass-Ceramic"; Dent Mater 2015, 31: 928-940.
Low et al; "Reduction in Dental Hypersensitivity With Nano-Hydroxyapatite, Potassium Nitrate, Sodium Monoflurophosphate and Antioxidants"; The Open Dentistry Journal; (2015), 9, pp. 92-97.
Marcolongo et al; "Surface Reaction Layer Formation in Vitro on a Bioactive Glass Fiber/Polymeric Composite"; J. Biomed Mater. Res.; (1997); 37, pp. 440-448.
Miglani et al; "Dentin Hypersensitivity: Recent Trends in Management"; J. Conserv. Dent. 2010; 13 (4) pp. 218-224.
Mintatoya et al; "Bioactive Glass Cloth That Propmotes New Bone Formation"; Key Eng. Mater.; (2013) 529-530; pp. 266-269.
Ramanujan, Book Chapter 17, Magnetic Particles for Biomedical Applications, R. Narayan (ed.), Biomedical Materials, DOI 10.1007/978-0-387-84872-3 17, C Springer Science+Business Media, LLC 2009, pp. 477-491.
Sglavo; "Chemical Strengthening of Soda Lime Silicate Float Glass: Effect of Small Differences in the KNO3 Bath," Int J Appl Glass Sci, 2015, 6: 72-82.
Simhan; "Chemical Durability of ZrO2 Containing Glasses"; Journal of Non-Crystalline Solids; 54 (1983) 335-343.
Singh et al; "Characterization of Si02—Na20—Fe203—Ca0—P205_B203 Glass Ceramics"; Journal of Materials Science: Materials in Medicine, 10(8) pp. 481-484. (1999.
International Search Report and Written Opinion PCT/US2017/034384 dated Aug. 7, 2017.
International Searching Authority Invitation to Pay Additional Fees Partial Search Report PCT/US2017/034409 dated Aug. 8, 2017.
International Search Report and Written Opinion PCT/US2017/034405 dated Jul. 21, 2017.
International Search Report and Written Opinion PCT/US2017/034421 dated Jul. 21, 2017.
Succaria et al; "Prescribing a Dental Ceramic Material: Zirconia Vs Lithium-Disilicate"; The Saudi Dent J, 2011, 23: 165-166.
Wallenberger et al; "The Liquidus Temperature; Its Critical Role in Glass Manufacturing"; International Journal of Applied Glass Science 1 [2] (2010) pp. 151-163.

(56) References Cited

OTHER PUBLICATIONS

Yao et al; "In Virto Bioactive Characteristics of Borate-Based Glasses With Controllable Degradation Behavior"; J. Am. Ceram. Soc.; 90 [1]; 303-306 (2007.
Yin et al; "Effect of ZrO2 on the Bioactivity Properties of Gel-Derived CaO—P2O5—SiO2—SrO Glasses"; Ceramics International; 43 (2017) pp. 9691-9698.
Yue et al; "Fiber Spinnability of Glass Melts"; International Journal of Applied Glass Science; (2016) pp. 1-11.
Zhang et al; "Chipping Resistance of Graded Zirconia Ceramics for Dental Crowns"; J Dent Res, 2012, 91:311315.
Harianawala et al. "Biocompatibility of Zirconia", J Adv Med Deni Sci Res 4(3) 2016, pp. 35-39.
Andersson et al. "In vivo behaviour of glasses in the SiO2—Na2O—CaO—P2O5—Al2O3—B2O3 system", J. Mat. Sci: Materials in Medicine (1990) 1: pp. 219-227.

\* cited by examiner

BIOACTIVE BOROPHOSPHATE GLASSES

This application claims the benefit of priority under 35 U.S.C. § 119 of U.S. Provisional Application Ser. No. 62/342,426 filed on May 27, 2016 the content of which is relied upon and incorporated herein by reference in its entirety.

CROSS-REFERENCE TO RELATED APPLICATIONS

The present application is related commonly owned and assigned USSN Provisional Application Nos., filed concurrently herewith:

62/342,384, entitled "BIOACTIVE ALUMINOBORATE GLASSES";

62/342,377, entitled "MAGNETIZABLE GLASS CERAMIC COMPOSITION AND METHODS THEREOF";

62/342,381, entitled "LITHIUM DISILICATE GLASS-CERAMIC COMPOSITIONS AND METHODS THEREOF";

62/342,391, entitled "BIODEGRADABLE MICROBEADS"; and

62/342,411, entitled "BIOACTIVE GLASS MICROSPHERES"; but does not claim priority thereto.

The present application is also related to commonly owned and assigned USSN Application Nos., 62/189,880, filed Jul. 7, 2015, entitled "ANTIMICROBIAL PHASE-SEPARATING GLASS AND GLASS CERAMIC ARTICLES AND LAMINATES," which mentions a copper containing laminate having a degradable phase, which phase liberates cooper ion, and a non-degradable phase.

The entire disclosure of each publication or patent document mentioned herein is incorporated by reference.

BACKGROUND

The disclosure relates to a glass composition, a bioactive glass composition, and to methods of making and using the compositions.

SUMMARY

In embodiments, the present disclosure provides:

a $CaO-B_2O_3-P_2O_5$ glass system including selected source additives;

a glass composition comprising, for example, 5 to 50% CaO, 0.1 to 80% $B_2O_3$, and 30 to 80% $P_2O_5$, based on a 100 mol % total of the composition;

a glass composition that can further comprise one or more source additives selected from, for example, 0.1 to 20% $Li_2O$, 0.1 to 20% $Na_2O$, 0.1 to 20% $K_2O$, 0.1 to 20% $Al_2O_3$, 0.1 to 10% ZnO, 0.1 to 11% MgO, 0.1 to 5% $Fe_2O_3$, 0.1 to 5% CuO, 0.1 to 5% $TiO_2$, and 0.1 to 20% $SiO_2$, based on a 100 mol % total of the composition;

a borophosphate glass composition where the addition of any of the source additives selected from the group $Li_2O$, $Na_2O$, $K_2O$, $Al_2O_3$, ZnO, MgO, $Fe_2O_3$, CuO, $TiO_2$, $SiO_2$, or combinations thereof, can control the degradation rates or dissolution rates of glass network formers (e.g., $B_2O_3$, $P_2O_5$, and $Al_2O_3$), and can improve the bioactivity properties of at least one of, for example, the biocompatibility, the angiogenesis, or both;

a borophosphate glass composition in the $CaO-B_2O_3-P_2O_5$ system having excellent biocompatibility and angiogenesis ability;

a borophosphate glass composition and a method of making where the addition of a source of $Al_2O_3$, $Na_2O$, or a mixture thereof, to the glass batch produces a glass product having improved biocompatibility; and a glass composition and a method of making where the addition of a source of $B_2O_3$ into a phosphate glass improves biocompatibility of the resulting glass.

BRIEF DESCRIPTION OF THE DRAWINGS

In embodiments of the disclosure.

DETAILED DESCRIPTION

Figure 1:
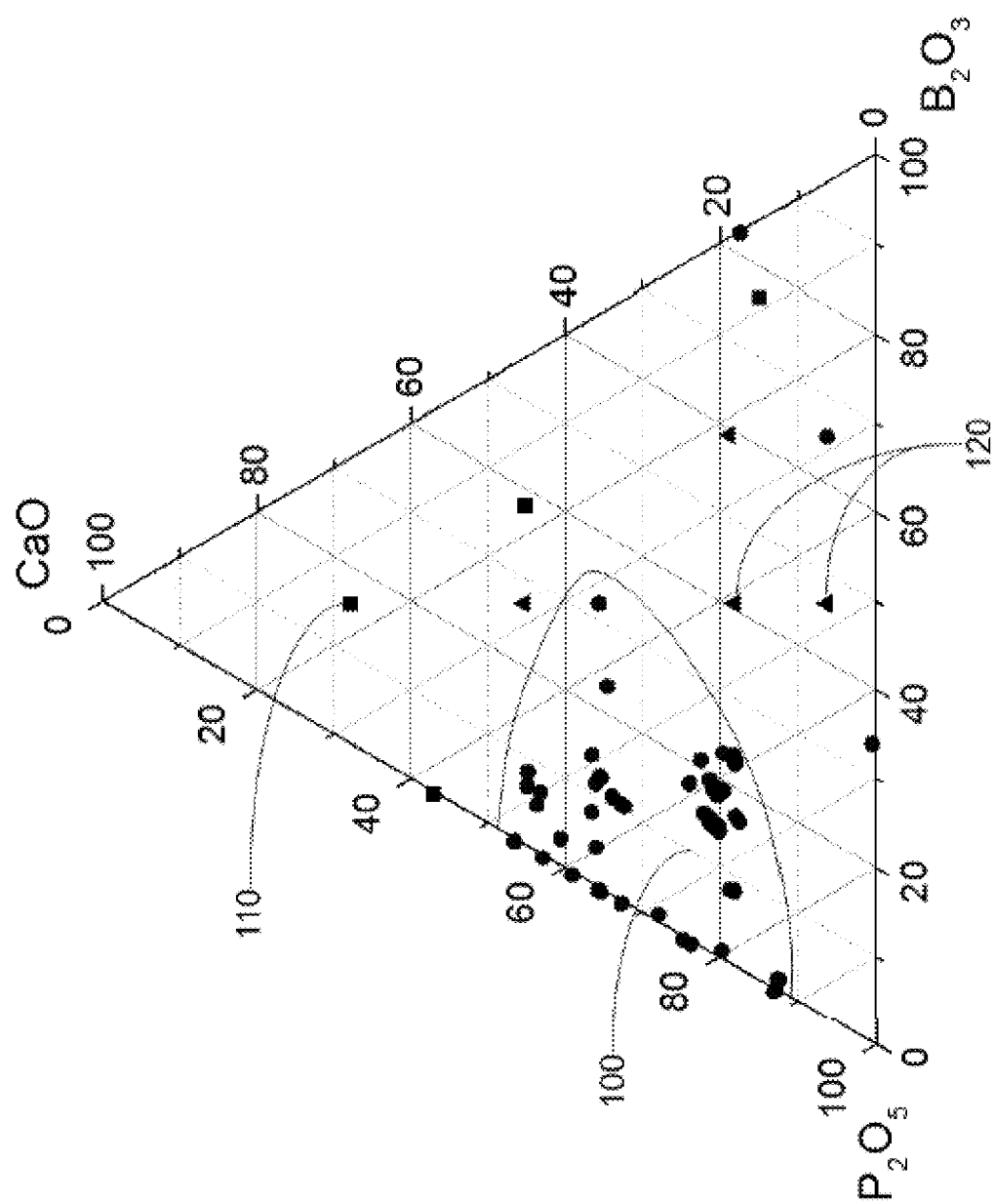
FIG. 1 shows a glass formability plot of the $CaO-P_2O_5-B_2O_3$ system with one or more source additives selected from, $Li_2O$, $Na_2O$, $K_2O$, $Al_2O_3$, ZnO, MgO, $Fe_2O_3$, CuO, $TiO_2$, and $SiO_2$.

Various embodiments of the disclosure will be described in detail with reference to drawings, if any. Reference to various embodiments does not limit the scope of the invention, which is limited only by the scope of the claims attached hereto. Additionally, any examples set forth in this specification are not limiting and merely set forth some of the many possible embodiments of the claimed invention.

In embodiments, the disclosed compositions, articles, and methods of making and using provide one or more advantageous features or aspects, including for example as discussed below. Features or aspects recited in any of the claims are generally applicable to all facets of the invention. Any recited single or multiple feature or aspect in any one claim can be combined or permuted with any other recited feature or aspect in any other claim or claims.

Definitions

"Biocompatibility," "biocompatible," or like terms refer to the ability of a material to perform with an appropriate host response in a specific situation, or alternatively, an ability to be in contact with a living system without producing an adverse effect.

"Angiogenesis ability," "angiogenic," "angiogenesis," or like terms, refer to the physiological process by which new blood vessels form from pre-existing vessels.

"Glass," "glasses," or like terms can refer to a glass or a glass-ceramic.

"Glass article," or like terms can refer to any object made wholly or partly of glass or a glass-ceramic.

"$CaO-B_2O_3-P_2O_5$ glass system," "$CaO-B_2O_3-P_2O_5$ composition(s) and additives," or like terms, refer to the three oxide component combination, alone or in combination with source additives, which defines the material space that produces the disclosed glass compositions.

"Glass network former," "glass former," "network glass former," "network former," or like terms refer to one or more of the disclosed batch ingredients, components, source materials, or starting materials, that form a glass network in the disclosed glass compositions. Examples of glass network formers can include, for example, $B_2O_3$, $P_2O_5$, and $Al_2O_3$. In embodiments, $P_2O_5$, is a primary glass network former since the ingredient results in a main phase, and $B_2O_3$ is a secondary glass network former because the ingredient results in a second phase that is less abundant than the main or primary phase. In embodiments, the network formers comprise the major components by mol % in the $CaO-B_2O_3-P_2O_5$ glass system.

"Additive," "source additive," "additive source," "source additive oxides," or like terms refer to one or more of the disclosed batch ingredients, batch components, or batch starting materials, which can be used to prepare the disclosed glass compositions. Examples of source additives can include, for example: $Li_2O$, $Na_2O$, $K_2O$, $Al_2O_3$, $ZnO$, $MgO$, $Fe_2O_3$, $CuO$, $TiO_2$, $SiO_2$, or mixtures thereof, based on a 100 mol % total of the composition. One of ordinary skill in the art will recognize that a source additive such as $Fe_2O_3$ can produce a mixture of $Fe_2O_3$ and $FeO$ (i.e., $Fe_2O_3/FeO$; $Fe_3O_4$), or $CuO$ can produce a mixture of $CuO$ and $Cu_2O$ (i.e., $CuO/Cu_2O$), resulting from, e.g., heating and thermal reduction in air.

"Include," "includes," or like terms means encompassing but not limited to, that is, inclusive and not exclusive.

"About" modifying, for example, the quantity of an ingredient in a composition, concentrations, volumes, process temperature, process time, yields, flow rates, pressures, viscosities, and like values, and ranges thereof, or a dimension of a component, and like values, and ranges thereof, employed in describing the embodiments of the disclosure, refers to variation in the numerical quantity that can occur, for example: through typical measuring and handling procedures used for preparing materials, compositions, composites, concentrates, component parts, articles of manufacture, or use formulations; through inadvertent error in these procedures; through differences in the manufacture, source, or purity of starting materials or ingredients used to carry out the methods; and like considerations. The term "about" also encompasses amounts that differ due to aging of a composition or formulation with a particular initial concentration or mixture, and amounts that differ due to mixing or processing a composition or formulation with a particular initial concentration or mixture.

"Optional" or "optionally" means that the subsequently described event or circumstance can or cannot occur, and that the description includes instances where the event or circumstance occurs and instances where it does not.

The indefinite article "a" or "an" and its corresponding definite article "the" as used herein means at least one, or one or more, unless specified otherwise.

Abbreviations, which are well known to one of ordinary skill in the art, may be used (e.g., "h" or "hrs" for hour or hours, "g" or "gm" for gram(s), "mL" for milliliters, and "rt" for room temperature, "nm" for nanometers, and like abbreviations).

Specific and preferred values disclosed for components, ingredients, additives, dimensions, conditions, times, and like aspects, and ranges thereof, are for illustration only; they do not exclude other defined values or other values within defined ranges. The composition and methods of the disclosure can include any value or any combination of the values, specific values, more specific values, and preferred values described herein, including explicit or implicit intermediate values and ranges.

Conventional bioactive glasses are silicate or borate based, and phosphorus is added as a dopant (e.g., less than 10 mol %) to promote the formation of hydroxyapatite and increase the bone tissue bonding capacity and bioactivity (see A. Tilocca, et al., "Structural effects of phosphorus inclusion in bioactive silicate glasses." *The Journal of Physical Chemistry* B 111, no. 51 (2007): 14256-14264). Compared to silicate- or borate-based bioactive glasses, there are relatively few studies on phosphate-based bioactive glasses, which have mainly focused on the $P_2O_5-Na_2O-CaO$ glass system (see K. Franks, et al., "The effect of MgO on the solubility behavior and cell proliferation in a quaternary soluble phosphate based glass system." *Journal of Materials Science: Materials in Medicine* 13, no. 6 (2002): 549-556; and I. Ahmed, et al., "Processing, characterisation and biocompatibility of iron-phosphate glass fibres for tissue engineering." *Biomaterials* 25, no. 16 (2004): 3223-3232.), and calcium phosphate ceramics (see H. Yuan, et al., "Osteoinduction by calcium phosphate biomaterials." *Journal of Materials Science: Materials in Medicine* 9, no. 12 (1998): 723-726; and J. Lu, et al., "The biodegradation mechanism of calcium phosphate biomaterials in bone." Journal of Biomedical Materials Research 63, no. 4 (2002): 408-412).

Components of calcium phosphate glasses or ceramics are present in the organic mineral phase of bone (hydroxycarbonate apatite), which makes these glasses have a chemical affinity with natural bone tissue (see M. N. Rahaman, et al., "Bioactive glass in tissue engineering." *Acta biomaterialia* 7, no. 6 (2011): 2355-2373). Moreover, through compositional modification, the solubility of phosphate glasses can be varied by several orders of magnitude (see B. C. Bunker, et al., "Phosphate glass dissolution in aqueous solutions." *Journal of Non-Crystalline Solids* 64, no. 3 (1984): 291-316), and ionic species released from glasses are also commonly found in the human body (see J. C. Knowles, "Phosphate based glasses for biomedical applications." *J Materials Chem.*, 13 (2003): 2395-2401; and M. Uo, et al., "Properties and cytotoxicity of water soluble $Na_2O-CaO-P_2O_5$ glasses," *Biomaterials* 19, no. 24 (1998): 2277-2284), which provides a broad range of degradation rates for various applications and less cytotoxicity. Accordingly, phosphate bioactive glasses have great potential in tissue engineering, cosmetics, health care area, and like applications (e.g., dental hypersensitivity treatment).

Some borate bioactive glasses have been shown to support cell proliferation and tissue infiltration (e.g., 13-93B3), but the potential toxicity of high concentration boron released from such glasses is a concern for borate glasses used for biomaterials (see M. N. Rahaman, supra.), which can cause developmental and reproductive toxicity (see F. J. Murray, "Issues in boron risk assessment: Pivotal study, uncertainty factors, and ADIs." *The Journal of Trace Elements in Experimental Medicine* 9, no. 4 (1996): 231-243), and a rapid release of boron from glass at the very beginning of the dissolution can cause acute toxicity to local cell growth and proliferation in vitro (see R. F. Brown, et al., "Effect of borate glass composition on its conversion to hydroxyapatite and on the proliferation of MC3T3-E1 cells." *Journal of Biomedical Materials Research* Part A 88, no. 2 (2009): 392-400). The addition of $B_2O_3$ into calcium phosphate glasses can increase formability of calcium phosphate glass and promote the formation of hydroxyapatite phase in SBF solution (see A. Saranti, et al., "Bioactive glasses in the system $CaO$—$B_2O_3$—$P_2O_5$: preparation, structural study and in vitro evaluation," *Journal of Non-Crystalline Solids* 352, no. 5 (2006): 390-398).

In embodiment, the present disclosure provides calcium borophosphate glass compositions having excellent biocompatibility and angiogenesis ability, which compositions were developed from the $CaO$—$B_2O_3$—$P_2O_5$ glass system with mixtures of glass network formers such as $B_2O_3$ and $P_2O_5$, or $B_2O_3$, $P_2O_5$, and $Al_2O_3$.

In embodiment, the present disclosure provides a borophosphate glass composition, comprising, for example:
0.1 to 80% $B_2O_3$,
30 to 80% $P_2O_5$, and
5 to 50% CaO, based on a 100 mol % total of the composition.

In embodiment, the borophosphate glass composition can further comprise at least one additive source selected from, for example: 0.1 to 20% $Li_2O$, 0.1 to 20% $Na_2O$, 0.1 to 20% $K_2O$, 0.1 to 20% $Al_2O_3$, more specifically 0.1 to 10% $Al_2O_3$, 0.1 to 10% ZnO, 0.1 to 11% MgO, 0.1 to 5% $Fe_2O_3$, 0.1 to 5% CuO, 0.1 to 5% $TiO_2$, 0.1 to 20% $SiO_2$, more specifically 0.1 to 10% $SiO_2$, and mixtures thereof, based on a 100 mol % total of the composition.

In embodiment, the borophosphate glass composition can be, for example, substantially free of at least one of $SiO_2$, SrO, or mixtures thereof.

In embodiment, any of the additive sources selected from the group of $Al_2O_3$, ZnO, MgO, $Fe_2O_3$, and CuO, can retard or inhibit the degradation rate or dissolution rate (i.e., going from a solid into a solution) of glass formers $B_2O_3$, $P_2O_5$, or both.

In embodiment, any of the additive sources selected from the group of $Li_2O$, $Na_2O$, $K_2O$, and $SiO_2$, can increase or accelerate the degradation rate or dissolution rate (i.e., going from a solid state into a solution state) of the composition. Dissolution rate, leach rate, or degradation rate are used to quantify the chemical durability of the disclosed inventive glasses. Weight loss measurement and ICP-OES solution analysis were used to measure the amount of glass and the amount of cations leached into solution from a solid.

In embodiment, the present disclosure provides a bioactive composition, comprising, for example:
a borophosphate glass composition comprising:
0.1 to 80% $B_2O_3$,
30 to 80% $P_2O_5$,
5 to 50% CaO, and
at least one additive selected from:
0.1 to 20% $Li_2O$,
0.1 to 20% $Na_2O$,
0.1 to 20% $K_2O$,
0.1 to 10% $Al_2O_3$,
0.1 to 10% ZnO,
0.1 to 11% MgO,
0.1 to 5% $Fe_2O_3$,
0.1 to 5% CuO, and mixtures thereof, based on a 100 mol % total of the composition; and
at least one live cell.
In embodiment, the at least one live cell can be selected, for example, from the group consisting of MC3T3 cells, MC3T3-E1 cells, human umbilical vein endothelial cells, or combinations thereof.

In embodiment, the source additive can be selected, for example, from the group of 0.1 to 20% $Li_2O$, 0.1 to 20% $Na_2O$, 0.1 to 20% $K_2O$, 0.1 to 20% $Al_2O_3$, more specifically 0.1 to 10% $Al_2O_3$, 0.1 to 10% ZnO, 0.1 to 11% MgO, 0.1 to 5% $Fe_2O_3$, 0.1 to 5% CuO, 0.1 to 5% $TiO_2$, 0.1 to 20% $SiO_2$, more specifically 0.1 to 10% $SiO_2$, and mixtures thereof, based on a 100 mol % total of the composition, and wherein the source additives improve the biocompatibility and the angiogenesis ability of the composition compared to a glass without the source additives for biocompatibility and compared to a glass without TCT for angiogenesis ability.

Figure 2:
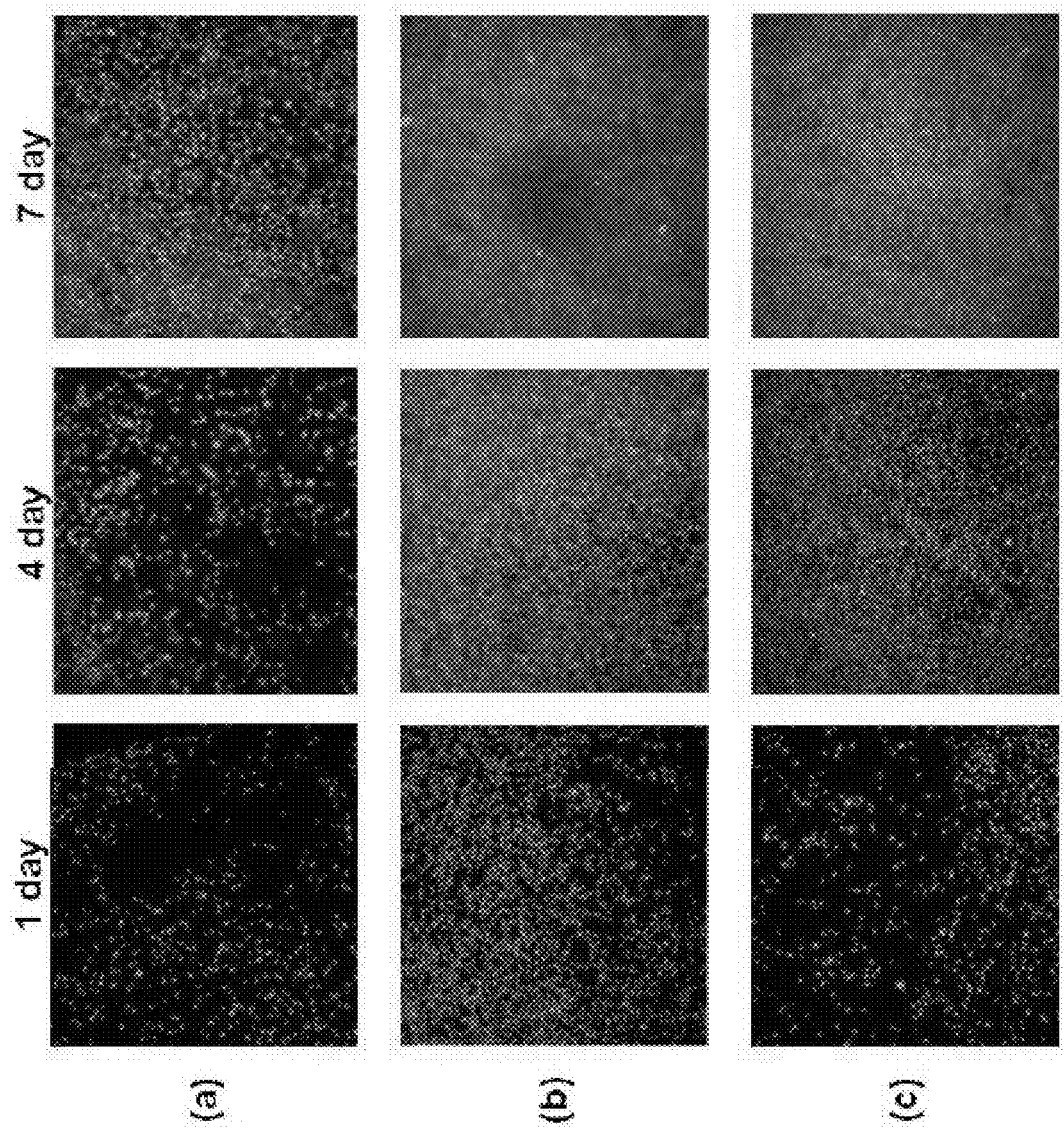
FIGS. 2A to 2C show time series optical images (low magnification of 2.5×) of MC3T3 cell seeded on the surface of selected polished glass discs.

In embodiment, the addition of 0.1 to 5.1 mol % $Al_2O_3$ as the source additive to the glass batch produces a glass product having improved biocompatibility compared to the same glass composition with the exception of being free of $Al_2O_3$ (see FIGS. 2A to 2C and Table 4). The number of cells was counted using ImageJ software and summarized in Table 4. The number of counted cells was normalized to the TCT control in Table 4. The images and cell counts showed that the addition of $Na_2O$ and $Al_2O_3$ clearly improved the cell growth.

In embodiment, the present disclosure provides an article of manufacture comprising at least one of the abovementioned borophosphate glass compositions.

In embodiment, the article of manufacture can further comprise, for example, at least one additive source selected from: 0.1 to 20% $Li_2O$, 0.1 to 20% $Na_2O$, 0.1 to 20% $K_2O$, 0.1 to 20% $Al_2O_3$, 0.1 to 10% ZnO, 0.1 to 11% MgO, 0.1 to 5% $Fe_2O_3$, 0.1 to 5% CuO, 0.1 to 5% $TiO_2$, 0.1 to 20% $SiO_2$, more specifically 0.1 to 10% $SiO_2$, and mixtures thereof, based on a 100% total of the composition.

In embodiment, the article of manufacture can further comprise, for example, at least one form factor selected from, for example: a cell culture article or apparatus; a cell phone cover glass component; a flat or curved, rigid or flexible, glass panel image display component; a structural glass component; a pharmaceutical drug dispensing vial component; a fiber optic component; and like form factors, or a combination thereof.

In embodiment, the disclosure provides a method of inhibiting the release of at least one of $B_2O_3$ and $P_2O_5$ species into an aqueous solution from a borophosphate glass composition including at least one additive source selected from the group of $Al_2O_3$, ZnO, MgO, $Fe_2O_3$, and CuO, the method of inhibiting comprising:
contacting the borophosphate glass composition with an aqueous solution.

In embodiment, an aqueous solution can be, for example, a simulated body fluid. In embodiment, the measured inhibition is relative to, or compared with, the same borophosphate glass composition but excludes (i.e., does not include) the at least one additive source selected from the group of $Al_2O_3$, ZnO, MgO, $Fe_2O_3$, and CuO.

In embodiment, the disclosure provides a method of increasing the release of at least one of $B_2O_3$ and $P_2O_5$ species into an aqueous solution from a disclosed borophosphate glass composition including at least one additive source selected from the group of $Li_2O$, $Na_2O$, $K_2O$, and $SiO_2$, comprising:
contacting the borophosphate glass composition with a liquid, such as water or an aqueous solution.

In embodiment, the liquid can be, for example, water, an aqueous solution, a simulated body fluid, and like liquids, or mixtures thereof.

In embodiment, an aqueous solution can instead be, for example, at least one of pure water, de-ionized water, tap water, saline, water having a dissolved salt, a mineral, a nutrient, a vitamin, a pharmaceutical, and like liquids, solutions, or suspensions.

In embodiment, the method can further comprise accomplishing the contacting in the presence of at least one live entity selected from: a cell; a tissue; an organ; a blood vessel; and like entities, or a combination thereof. In embodiment, the contacting enhances the bioactivity interaction properties of the composition and the live entity for at least one of: the biocompatibility; the angiogenesis; or both the biocompatibility and the angiogenesis.

In embodiment, the disclosure provides a method of proliferating cells on a disclosed bioactive glass composition in an aqueous solution comprising:

contacting the abovementioned disclosed bioactive glass composition and the at least one live cell, or the at least one live entity, in the aqueous solution for a time sufficient to proliferate the at least one live cell, or the at least one live entity.

In embodiment, the aqueous solution can be, for example, a simulated body fluid, or like simulated, synthetic, or natural biological fluid.

In embodiments, the present disclosure is advantaged in several aspects, including for example:

the disclosed glass compositions and the disclosed bioactive compositions have relatively low melting temperatures;

the relatively low melting temperatures translate into reduced manufacturing costs for disclosed glass compositions;

the disclosed glass compositions in the $CaO-B_2O_3-P_2O_5$ system have excellent biocompatibility and angiogenesis ability; and the addition of a source of $Al_2O_3$, $Na_2O$, or mixtures thereof, to the glass batch produces the disclosed glass compositions as a product having improved bioactivity.

In embodiments, the disclosure provides glass compositions in the calcium borophosphate system that exhibit excellent biocompatibility and angiogenesis ability.

In embodiments, the disclosure provides glass compositions related to the $CaO-B_2O_3-P_2O_5$ glass system having one or more of the disclosed additives.

In embodiments, the disclosure provides $CaO-B_2O_3-P_2O_5$ glass system compositions having various disclosed source additive oxides or product oxide mixtures including, for example, at least one of $Li_2O$, $Na_2O$, $K_2O$, $Al_2O_3$, ZnO, MgO, $Fe_2O_3$/FeO (e.g., $Fe_3O_4$), $CuO/Cu_2O$, $TiO_2$, $SiO_2$, or mixtures thereof, that can control the degradation rates of the glass, and improve the bioactivity and angiogenesis ability of the glass.

In embodiments, the disclosure provides glass compositions comprising, for example, 5 to 50% CaO, 0.1 to 80% $B_2O_3$, and 30 to 80% $P_2O_5$, based on a 100 mol % total of the composition.

In embodiments, the disclosure provides glass compositions that can further comprise, for example, 0.1 to 20% $Li_2O$, 0.1 to 20% $Na_2O$, 0.1 to 20% $K_2O$, 0.1 to 20% $Al_2O_3$, 0.1 to 10% ZnO, 0.1 to 11% MgO, 0.1 to 5% $Fe_2O_3$/FeO, 0.1 to 5% $CuO/Cu_2O$, 0.1 to 5% $TiO_2$, 0.1 to 20% $SiO_2$, or mixtures thereof, based on a 100 mol % total of the composition.

In embodiments, the disclosure provides glass compositions that can further comprise the presence or absence of one or more additives selected from, for example: 0 to 20% $Li_2O$, 0 to 20% $Na_2O$, 0 to 20% $K_2O$, 0 to 10% $Al_2O_3$, 0 to 10% ZnO, 0 to 10% MgO, 0 to 5% $Fe_2O_3$/FeO, and 0 to 5% $CuO/Cu_2O$, 0 to 5% $TiO_2$, 0 to 10% $SiO_2$, and mixtures thereof, based on a 100 mol % total of the composition.

In embodiments, the disclosure provides glass compositions having excellent biocompatibility and angiogenesis ability. The excellent biocompatibility and angiogenesis ability properties were demonstrated for representative disclosed glass compositions having the disclosed glass physical properties including strain temperature, annealing temperature, softening temperature, coefficient of thermal expansion (CTE) less than 300° C. on heating, Young's modulus, shear modulus, and Poisson's ratio (i.e., the coefficient of expansion on the transverse axial, which is the negative ratio of transverse to axial strain).

In embodiments, the disclosure provides a method of increasing the Young's modulus and the shear modulus of a $CaO-B_2O_3-P_2O_5$ glass composition comprising: including at least one of $Li_2O$, $Al_2O_3$, $TiO_2$, or mixtures thereof, in the batch composition or the melt composition.

Representative glass compositions and properties are summarized in Tables 1 and 2, respectively. Table 1 lists disclosed examples of glass compositions in the $CaO-B_2O_3-P_2O_5$ system. Glasses were made from batches (e.g., glass melts of 1000 g 100% theoretical yield; typical yields were about 900 g or 90 wt % due to, e.g., mechanical loss) of source or starting materials including, for example, $Ca_2P_2O_7$ (Alfa Aesar, 96%), $CaCO_3$ (Fisher Scientific, 99.9%), $B_2O_3$ (Chemical Distributors Inc., 98.69%), phosphoric acid (liquid, VWR Scientific, 85-88%), $LiH_2PO_4$ (BassTech International), $Na_2CO_3$ (Fisher Scientific, 99.99%), $NaPO_3$ (Alfa Aesar), $KH_2PO_4$ (Alfa Aesar, 98+%), $Al_2O_3$ (Almatis, 99.78%), $Zn_2P_2O_7$ (Pfaltz & Bauer), $Mg(H_2PO_4)_2$ (BassTech International), $FePO_4 \cdot 2H_2O$ (Alfa Aesar), CuO (American Chemet, 99.8%), $TiO_2$ (Harry W Gaffney, 99.68%), and sodium silicate (PQ Corporation) that were melted in Pt crucibles at from 1200° C. to 1500° C. in air with an aluminum cover.

Table 1 lists examples of disclosed glass compositions in the $CaO-P_2O_5-B_2O_3$ system with one or more source additives selected from, $Li_2O$, $Na_2O$, $K_2O$, $Al_2O_3$, ZnO, MgO, $Fe_2O_3$, CuO, $TiO_2$, and $SiO_2$. Examples 1 to 65 are glasses that were formed and are represented by solid dots or solid circles in FIG. 1. Examples 66 to 69 are glasses that crystallized or phase separated during cooling and are represented by solid triangles in FIG. 1. Examples 70 to 73 are non-glass formation compositions and are represented by solid squares in FIG. 1 (i.e., the composition was not pourable since it was still a solid at about 1500° C.). The compositions were analyzed with the exception that: the concentration of the $P_2O_5$ was determined by the difference from the analyzed concentration of other components; and the mol % for the compositions is based on the batched composition. A composition designated by "C-(#)" is a control composition (e.g., C-29), which control composition is compositionally outside the $CaO-P_2O_5-B_2O_3$ system but may nevertheless be inventive.

TABLE 1

Examples of disclosed glass compositions.

| Example # | CaO | $B_2O_3$ | $P_2O_5$ | $Li_2O$ | $Na_2O$ | $K_2O$ | $Al_2O_3$ | ZnO | MgO | $Fe_2O_3$ | CuO | $TiO_2$ | $SiO_2$ |
|---|---|---|---|---|---|---|---|---|---|---|---|---|---|
| 1 | 23.6 | 17.9 | 58.6 | | | | | | | | | | |
| 2[a] | 21.4 | 15.4 | 63.2 | | | | | | | | | | |
| 3[a] | 20.9 | 19.6 | 59.5 | | | | | | | | | | |
| 4[a] | 19.0 | 18.2 | 58.1 | 4.7 | | | | | | | | | |
| 5[a] | 17.0 | 16.9 | 53.7 | 12.4 | | | | | | | | | |
| 6 | 36.8 | 6.2 | 42.7 | 8.8 | | | 5.5 | | | | | | |
| 7 | 29.7 | 10.9 | 44.4 | 10.0 | | | 5.0 | | | | | | |
| 8 | 14.9 | 20.0 | 50.3 | 9.8 | | | 5.0 | | | | | | |
| 9 | 15.2 | 7.5 | 63.5 | 8.6 | | | 5.1 | | | | | | |
| 10 | 29.7 | 10.9 | 43.8 | 9.6 | | | 5.0 | | | | | 1.0 | |
| 11 | 15.0 | 20.3 | 49.2 | 9.5 | | | 5.0 | | | | | 1.0 | |
| 12 | 15.4 | 7.2 | 61.5 | 9.7 | | | 5.1 | | | | | 1.0 | |
| 13[a] | 18.9 | 17.6 | 58.9 | | | | 4.7 | | | | | | |
| 14[a] | 17.9 | 17.0 | 56.2 | | | | 8.9 | | | | | | |
| 15[a] | 17.6 | 16.3 | 53.1 | | | | 13.0 | | | | | | |
| 16[a] | 17.0 | 15.8 | 50.5 | | | | 16.6 | | | | | | |
| 17[a] | 16.7 | 16.8 | 53.8 | | 12.7 | | | | | | | | |
| 18[a] | 16.1 | 16.2 | 51.7 | | 16.0 | | | | | | | | |
| C-19[b,c] | — | 29.0 | 56.0 | | 10.0 | | 5.0 | | | | | | |
| 20[b] | 5.0 | 56.0 | 24.0 | | 10.0 | | 5.0 | | | | | | |
| 21[b] | 30.0 | 27.5 | 27.5 | | 10.0 | | 5.0 | | | | | | |
| 22 | 36.6 | 4.7 | 43.0 | | 10.5 | | 5.1 | | | | | | |
| 23 | 30.3 | 10.0 | 44.4 | | 10.2 | | 5.0 | | | | | | |
| 24 | 14.9 | 19.6 | 50.4 | | 10.0 | | 5.0 | | | | | | |
| 25 | 15.0 | 7.5 | 62.4 | | 10.1 | | 5.0 | | | | | | |
| C-26 | 14.4 | 70.6 | — | | 10.2 | | 4.7 | | | | | | |
| 27 | 38.1 | 6.0 | 41.3 | | 9.9 | | 4.7 | | | | | | |
| 28 | 29.5 | 20.3 | 36.5 | | 9.4 | | 4.2 | | | | | | |
| C-29 | 29.8 | — | 54.5 | | 5.4 | 5.1 | | 2.4 | 2.9 | | | | |
| 30 | 30.0 | 3.9 | 50.1 | | 5.6 | 5.2 | | 2.4 | 2.9 | | | | |
| 31 | 30.5 | 7.0 | 46.6 | | 5.5 | 5.0 | | 2.4 | 2.9 | | | | |
| 32 | 30.4 | 12.4 | 41.1 | | 5.6 | 5.2 | | 2.4 | 2.9 | | | | |
| 33 | 37.5 | 7.3 | 39.3 | | 5.5 | 5.1 | | 2.3 | 2.9 | | | | |
| C-34 | 19.5 | — | 60.5 | | 6.8 | 6.5 | | 3.0 | 3.6 | | | | |
| 35 | 23.3 | 1.0 | 60.3 | | 5.2 | 4.8 | | 2.4 | 3.0 | | | | |
| 36 | 16.2 | 1.0 | 66.4 | | 5.6 | 5.2 | | 2.6 | 3.1 | | | | |
| 37 | 9.7 | 1.3 | 69.2 | | 6.8 | 6.4 | | 3.0 | 3.6 | | | | |
| 38[a] | 27.7 | 9.5 | 48.3 | | 3.0 | 2.2 | | 6.6 | 2.6 | | | | |
| 39[a] | 27.5 | 9.5 | 48.9 | | 3.2 | 2.2 | | 8.8 | | | | | |
| 40[a] | 28.6 | 9.7 | 47.1 | | 2.5 | 2.2 | | 2.2 | 7.7 | | | | |
| 41[a] | 28.6 | 9.7 | 46.7 | | 2.3 | 2.2 | | | 10.5 | | | | |
| 42[a] | 18.9 | 18.3 | 48.6 | | 4.9 | 4.5 | | 2.2 | 2.6 | | | | |
| 43[a] | 15.5 | 15.2 | 57.6 | | | 11.7 | | | | | | | |
| 44[a] | 14.6 | 14.4 | 56.6 | | | 14.3 | | | | | | | |
| 45 | 18.6 | 13.5 | 58.4 | | 9.2 | | | | | 0.4 | | | |
| 46 | 18.2 | 13.2 | 58.5 | | 8.9 | | | | | 1.2 | | | |
| 47 | 18.4 | 13.1 | 57.4 | | 9.0 | | | | | 2.1 | | | |
| 48 | 18.4 | 13.3 | 58.9 | | 9.0 | | | | | | 0.5 | | |
| 49 | 18.7 | 13.3 | 57.7 | | 8.9 | | | | | | 1.4 | | |
| 50 | 17.6 | 13.3 | 57.9 | | 8.9 | | | | | | 2.2 | | |
| 51[a] | 21.6 | 15.4 | 62.5 | | | | | | | | 0.5 | | |
| 52[a] | 20.8 | 15.1 | 62.5 | | | | | | | | 1.6 | | |
| 53[a] | 20.4 | 14.8 | 62.2 | | | | | | | | 2.6 | | |
| 54[a] | 19.5 | 14.2 | 61.3 | | | | | | | | 5.0 | | |
| 55[a] | 17.1 | 12.5 | 57.2 | | 8.8 | | | | | | 4.3 | | |
| 56 | 15.4 | 20.2 | 50.2 | | 10.0 | | | | | | | | 4.2 |
| 57 | 16.0 | 19.6 | 47.7 | | 9.4 | | | | | | | | 7.3 |
| C-58 | 45.4 | — | 52.7 | | | | | | | | | | 1.9 |
| C-59 | 39.9 | — | 53.7 | | | | | | | | | | 6.4 |
| C-60 | 35.3 | — | 55.7 | | | | | | | | | | 9.0 |
| C-61 | 30.3 | — | 56.3 | | | | | | | | | | 13.4 |
| C-62 | 26.3 | — | 55.0 | | | | | | | | | | 18.6 |
| C-63 | 19.9 | — | 65.4 | | | | 14.7 | | | | | | |
| C-64 | 10.1 | — | 70.1 | | | | 19.8 | | | | | | |
| 65 | 40.3 | 3.3 | 56.4 | | | | | | | | | | |
| 66[b] | 5.0 | 40.0 | 40.0 | | 10.0 | | 5.0 | | | | | | |
| 67[b] | 15.0 | 35.0 | 35.0 | | 10.0 | | 5.0 | | | | | | |
| 68[b] | 38.2 | 23.4 | 23.4 | | 10.0 | | 5.0 | | | | | | |
| 69 | 15.5 | 50.5 | 18.4 | | 10.3 | | 5.2 | | | | | | |
| 70[b] | 57.5 | 13.8 | 13.8 | | 10.0 | | 5.0 | | | | | | |
| 71[b] | 38.3 | 32.7 | 14.0 | | 10.0 | | 5.0 | | | | | | |

TABLE 1-continued

Examples of disclosed glass compositions.

| Example # | CaO | B₂O₃ | P₂O₅ | Li₂O | Na₂O | K₂O | Al₂O₃ | ZnO | MgO | Fe₂O₃ | CuO | TiO₂ | SiO₂ |
|---|---|---|---|---|---|---|---|---|---|---|---|---|---|
| C-72[b] | 48.3 | — | 36.7 | | 10.0 | | 5.0 | | | | | | |
| 73 | 12.2 | 65.2 | 7.1 | | 10.4 | | 5.1 | | | | | | |

[a] the concentration of $P_2O_5$ is by difference from the analyzed concentration of the other components.

[b] a batched composition.

[c] "C-#" designates a control composition. A "C-#" control composition is not believed to be a prior art comparative example but may reside outside of the disclosed $CaO-B_2O_3-P_2O_5$ glass system compositions for lack of at least one $CaO-B_2O_3-P_2O_5$ component.

TABLE 2

Glass properties.

| Example # | Strain (° C.) | Annealing (° C.) | Softening (° C.) | CTE ($10^{-6}$ or ppm/° C.) (deviation) | Young's Modulus (Mpsi) | Shear Modulus (Mpsi) | Poisson's Ratio |
|---|---|---|---|---|---|---|---|
| 1 | 474.9 | 507.8 | 751.3 | 7.67(2) | | | |
| 2 | 407.4 | 449.3 | 632.4 | 8.92(2) | 8.07 | 3.30 | 0.223 |
| 3 | 498.8 | 544.3 | 735.4 | 8.51(2) | 8.74 | 3.62 | 0.209 |
| 6 | 450.3 | 479.7 | 581.2 | 10.33(4) | | | |
| 7 | 446.5 | 477.8 | 588 | 9.77(4) | | | |
| 9 | 395.4 | 429.8 | 579.6 | 9.68(4) | | | |
| 10 | | | 598 | | 11.16 | 4.48 | 0.245 |
| 11 | | | | | 11.41 | 4.7 | 0.214 |
| 12 | 411.6 | 447.9 | 599.6 | 9.38(3) | | | |
| 13 | 553.0 | 595.8 | 772.9 | 7.85(2) | 10.06 | 4.13 | 0.217 |
| 14 | 570.6 | 613.4 | 782.0 | 7.29(2) | 10.56 | 4.35 | 0.214 |
| 15 | 580.3 | 621.6 | 776.8 | 6.74(2) | 10.47 | 4.29 | 0.219 |
| 22 | 463.6 | 499 | 606.5 | 9.58(3) | | | |
| 23 | 464.3 | 495.5 | 607.9 | 11.26(4) | 10.14 | 4.06 | 0.248 |
| 24 | 462.6 | 495.3 | 644.1 | 10.63(3) | 10.38 | 4.24 | 0.225 |
| 25 | 521.2 | 565.2 | 581.4 | 8.85(2) | 8.49 | 3.45 | 0.231 |
| C-26 | 393.5 | 428.9 | 622 | 10.58(3) | 9.09 | 3.6 | 0.261 |
| 27 | | | 601.9 | | | | |
| C-29 | 348.3 | 378.9 | 491.7 | 12.32(3) | | | |
| 30 | 409.3 | 441.7 | 501.6 | 12.02(4) | | | |
| 31 | 434.4 | 467.2 | 582.4 | 11.67(5) | 9.16 | 3.66 | 0.251 |
| 32 | 464.5 | 499 | 611.5 | 11.19(5) | | | |
| 33 | 443.9 | 476.4 | 554.7 | 12.17(4) | | | |
| C-34 | 384.7 | 420 | 570.7 | 11.29(5) | 8.1 | 3.28 | 0.234 |
| 35 | 376.4 | 410 | | | | | |
| 36 | 328.4 | 361.3 | 584.5 | | 6.85 | 2.76 | 0.24 |
| 37 | 312.6 | 346.8 | 488.2 | 12.51(4) | | | |
| 45 | | | 545.1 | | | | |
| 46 | | | 559.6 | | 8.04 | 3.33 | 0.207 |
| 47 | | | 568.1 | | 8.36 | 3.41 | 0.228 |
| 48 | | | 545.7 | | 7.84 | 3.18 | 0.231 |
| 49 | | | 541.9 | | 7.98 | 3.23 | 0.235 |
| 50 | | | 549.1 | | 8.12 | 3.32 | 0.225 |
| 51 | 422.6 | 465.4 | 654.9 | 9.03(2) | 8.15 | 3.35 | 0.218 |
| 52 | 415.4 | 456.7 | 643.8 | 9.36(3) | 8.12 | 3.35 | 0.213 |
| 53 | 362.2 | 397.3 | 646.3 | 9.16(2) | 8.26 | 3.41 | 0.213 |
| 54 | 412.5 | 453.7 | 642.0 | 9.10(2) | 8.41 | 3.44 | 0.223 |
| 55 | | | 549.1 | 10.46(2) | 8.27 | 3.36 | 0.232 |
| 56 | 431.3 | 468.9 | 625.6 | 10.17(3) | | | |
| 57 | 437.0 | 474.6 | 632.7 | 10.00(3) | | | |
| C-58 | 456.4 | 490.5 | 606.7 | 9.84(2) | 7.78 | 3.1 | 0.257 |
| C-59 | 453.8 | 489.4 | 609.9 | 9.54(2) | 7.96 | 3.19 | 0.247 |
| C-60 | 469.1 | 505.1 | 629.6 | 8.98(2) | 8.19 | 3.3 | 0.243 |
| C-61 | 483.0 | 520.0 | 648.6 | 8.67(2) | 8.52 | 3.43 | 0.241 |
| C-62 | 501.6 | 538.9 | 667.3 | 8.35(2) | 8.79 | 3.57 | 0.231 |
| C-63 | 552.0 | 590.7 | 739.6 | 7.42(2) | 10.19 | 4.18 | 0.22 |

TABLE 2-continued

Glass properties.

| Example # | Strain (° C.) | Annealing (° C.) | Softening (° C.) | CTE ($10^{-6}$ or ppm/° C.) (deviation) | Young's Modulus (Mpsi) | Shear Modulus (Mpsi) | Poisson's Ratio |
|---|---|---|---|---|---|---|---|
| C-64 | 620.4 | 659.7 | 816.6 | 6.80(2) | 11.52 | 4.78 | 0.205 |
| 65 | 415.8 | 451.1 | 582.1 | 10.05(2) | 8.05 | 3.21 | 0.255 |

TABLE 3

Reagents for simulated body fluid (SBF) (pH 7.4 at 37° C., 1 L).

| Order | Reagents | Amount |
|---|---|---|
| 1 | NaCl | 7.996 g |
| 2 | NaHCO$_3$ | 0.350 g |
| 3 | KCl | 0.224 g |
| 4 | K$_2$HPO$_4$•3H$_2$O | 0.228 g |
| 5 | MgCl$_2$•6H$_2$O | 0.305 g |
| 6 | 1M HCl* | maximum 40 mL |
| 7 | CaCl$_2$ | 0.278 g |
| 8 | Na$_2$SO$_4$ | 0.071 g |
| 9 | (CH$_2$OH)$_3$CNH$_2$ | 6.057 g |

*HCl is used to adjust pH of the SBF solution, and about 90 vol % of total amount of HCl is added. If the pH reaches 7.40 at 37° C. at 90 vol % HCl, the remaining 10 vol % HCl is not added.

TABLE 4

Biocompatibility of selected compositions tested with MC3T3-E1 cells, and the angiogenesis ability tested with HUVEC-2 cell. The number was normalized to TCT control.

| Example # | Biocompatibility MC3T3-E1 cell amount at day 1 | | Angiogenesis HUVEC-2 cell loops amount | |
|---|---|---|---|---|
| | Average | STDEV | Average | STDEV |
| 1 | 95 | 9 | 156 | 9 |
| 10 | 104 | 36 | 77 | 19 |
| 22 | 180 | 10 | 146 | 16 |
| 23 | 314 | 29 | 131 | 29 |
| 24 | 335 | 33 | 155 | 9 |
| 25 | 175 | 24 | 147 | 12 |
| C-26 | | | 62 | 5 |
| 27 | <5 | | 111 | 13 |
| C-29 | 7 | 1 | 281 | 23 |
| 30 | 92 | 9 | 116 | 9 |
| 31 | 211 | 21 | 221 | 18 |
| 32 | 194 | 19 | 212 | 17 |
| 33 | 104 | 11 | 49 | 4 |
| C-34 | 120 | 14 | 216 | 17 |
| 35 | <5 | | 216 | 17 |
| 36 | 175 | 23 | 205 | 16 |
| 37 | 133 | 17 | 170 | 14 |
| 45 | <5 | | 99 | 8 |
| 46 | 94 | 22 | 135 | 9 |
| 47 | 60 | 24 | 132 | 22 |
| 48 | 49 | 9 | 95 | 12 |
| 49 | 76 | 42 | 77 | 6 |
| 50 | 69 | 19 | 81 | 24 |
| C-58 | <5 | | 95 | 20 |
| C-59 | <5 | | 93 | 12 |
| C-60 | <5 | | 100 | 22 |
| C-61 | <5 | | 110 | 6 |
| C-62 | <5 | | 96 | 10 |
| C-63 | <5 | | 88 | 18 |
| C-64 | <5 | | 104 | 14 |
| 65 | <5 | | 103 | 18 |

In embodiment, the inventive bioactive compositions can be, for example, selected from exemplary compositions 1, 10, 22, 23, 24, 25, 30, 31, 32, 33, C-34, 36, 37 and 46 listed in Table 1 and excerpted to Table 5. These compositions had superior or comparable biocompatibility compared to a TCT control.

TABLE 5

Bioactive compositions having superior or comparable biocompatibility.

| Example # | CaO | B$_2$O$_3$ | P$_2$O$_5$ | Li$_2$O | Na$_2$O | K$_2$O | Al$_2$O$_3$ | ZnO | MgO | Fe$_2$O$_3$ | CuO | TiO$_2$ | SiO$_2$ |
|---|---|---|---|---|---|---|---|---|---|---|---|---|---|
| 1 | 23.6 | 17.9 | 58.6 | | | | | | | | | | |
| 10 | 29.7 | 10.9 | 43.8 | 9.6 | | | 5.0 | | | | | 1.0 | |
| 22 | 36.6 | 4.7 | 43.0 | | 10.5 | | 5.1 | | | | | | |
| 23 | 30.3 | 10.0 | 44.4 | | 10.2 | | 5.0 | | | | | | |
| 24 | 14.9 | 19.6 | 50.4 | | 10.0 | | 5.0 | | | | | | |
| 25 | 15.0 | 7.5 | 62.4 | | 10.1 | | 5.0 | | | | | | |
| 30 | 30.0 | 3.9 | 50.1 | | 5.6 | 5.2 | | 2.4 | 2.9 | | | | |
| 31 | 30.5 | 7.0 | 46.6 | | 5.5 | 5.0 | | 2.4 | 2.9 | | | | |
| 32 | 30.4 | 12.4 | 41.1 | | 5.6 | 5.2 | | 2.4 | 2.9 | | | | |
| 33 | 37.5 | 7.3 | 39.3 | | 5.5 | 5.1 | | 2.3 | 2.9 | | | | |
| C-34 | 19.5 | — | 60.5 | | 6.8 | 6.5 | | 3.0 | 3.6 | | | | |
| 36 | 16.2 | 1.0 | 66.4 | | 5.6 | 5.2 | | 2.6 | 3.1 | | | | |
| 37 | 9.7 | 1.3 | 69.2 | | 6.8 | 6.4 | | 3.0 | 3.6 | | | | |
| 46 | 18.2 | 13.2 | 58.5 | | 8.9 | | | | | 1.2 | | | |

In embodiment, the bioactive compositions can be, for example, selected from exemplary compositions 1, 10, 22, 23, 24, 25, 27, 30, 31, 32, 33, 35, 36, 37, 45, 46, 47, 48, and 65, listed in Table 1 and excerpted to Table 6. The inventive control compositions C-29, C-34, C-58, C-59, C-60, C-61, C-62, and C-64, were not biocompatible but had comparable (e.g., C-61) or superior (e.g., C-29) angiogenic ability. These inventive compositions had comparable or superior angiogenic ability compared to a TCT control.

FIGS. 2A and 2B presents two examples of live cell staining images, in which composition 1 is the base glass containing only $CaO$—$P_2O_5$—$B_2O_3$ without additives (FIG. 2A); and composition 24 was similar to composition 1 with the exception of the addition of $Na_2O$ and $Al_2O_3$ (FIG. 2B). Cell attachment results demonstrate that the addition or inclusion of $Na_2O$ and $Al_2O_3$ in the composition clearly improves the cell growth (FIG. 2A time series v. FIG. 2b time series). FIG. 2C shows optical images of MC3T3 cell

TABLE 6

Bioactive compositions having superior or comparable angiogenesis.

| Example # | CaO | $B_2O_3$ | $P_2O_5$ | $Li_2O$ | $Na_2O$ | $K_2O$ | $Al_2O_3$ | ZnO | MgO | $Fe_2O_3$ | CuO | $TiO_2$ | $SiO_2$ |
|---|---|---|---|---|---|---|---|---|---|---|---|---|---|
| 1 | 23.6 | 17.9 | 58.6 | | | | | | | | | | |
| 10 | 29.7 | 10.9 | 43.8 | 9.6 | | | 5.0 | | | | | 1.0 | |
| 22 | 36.6 | 4.7 | 43.0 | | 10.5 | | 5.1 | | | | | | |
| 23 | 30.3 | 10.0 | 44.4 | | 10.2 | | 5.0 | | | | | | |
| 24 | 14.9 | 19.6 | 50.4 | | 10.0 | | 5.0 | | | | | | |
| 25 | 15.0 | 7.5 | 62.4 | | 10.1 | | 5.0 | | | | | | |
| 27 | 38.1 | 6.0 | 41.3 | | 9.9 | | 4.7 | | | | | | |
| 30 | 30.0 | 3.9 | 50.1 | | 5.6 | 5.2 | | 2.4 | 2.9 | | | | |
| 31 | 30.5 | 7.0 | 46.6 | | 5.5 | 5.0 | | 2.4 | 2.9 | | | | |
| 32 | 30.4 | 12.4 | 41.1 | | 5.6 | 5.2 | | 2.4 | 2.9 | | | | |
| 33 | 37.5 | 7.3 | 39.3 | | 5.5 | 5.1 | | 2.3 | 2.9 | | | | |
| 35 | 23.3 | 1.0 | 60.3 | | 5.2 | 4.8 | | 2.4 | 3.0 | | | | |
| 36 | 16.2 | 1.0 | 66.4 | | 5.6 | 5.2 | | 2.6 | 3.1 | | | | |
| 37 | 9.7 | 1.3 | 69.2 | | 6.8 | 6.4 | | 3.0 | 3.6 | | | | |
| 45 | 18.6 | 13.5 | 58.4 | | 9.2 | | | | | 0.4 | | | |
| 46 | 18.2 | 13.2 | 58.5 | | 8.9 | | | | | 1.2 | | | |
| 47 | 18.4 | 13.1 | 57.4 | | 9.0 | | | | | 2.1 | | | |
| 48 | 18.4 | 13.3 | 58.9 | | 9.0 | | | | | | 0.5 | | |
| 65 | 40.3 | 3.3 | 56.4 | | | | | | | | | | |

Referring to the Figures, FIG. 1 shows a glass formability plot of the $CaO$—$P_2O_5$—$B_2O_3$ system with one or more source additives selected from, for example, $Li_2O$, $Na_2O$, $K_2O$, $Al_2O_3$, ZnO, MgO, $Fe_2O_3$, CuO, $TiO_2$, $SiO_2$, and mixtures thereof. The total concentration of $CaO$—$P_2O_5$—$B_2O_3$ was normalized to 100 in the plot. FIG. 1 shows the glass formation in phosphate-rich region (100) (area bounded approximately by the arc in triangle's left corner) is larger than the borate-rich area (right corner). A small addition of B2O3 (e.g., about 4 mol %) improves the glass formability of calcium metaphosphate, and like species. Non-glass formation compositions are indicated with squares in FIG. 1, such as Ca9(AlPO4)7 (110). A crystalline phase BPO4 (120) formed for the composition close to B/P ratio=1. Measured glass properties are listed in Table 2. Biocompatibility and bioactivity were evaluated for compositions in this system by testing with MC3T3-E1 cells (an osteoblast precursor cell line) attachment experiments. Six compositions (compositions 1, 10, 24, 31, 32, and 46) in the phosphate-rich area show good cell attachment and proliferation performance, which are comparable or even better than controls (i.e., tissue culture treated plastic plates and gelatin coated lab glassware), and also lead to less cell death, even under circumstance of no daily medium change after the cells were seeded. Compared to the control, no obvious cell toxicity was observed for glasses in this system.

FIGS. 2A and 2C show time series optical images (low magnification of 2.5×) of MC3T3-E1 cells seeded on the surface of polished glass discs (12.5 mm in diameter×2.0 mm thickness) placed in wells of 24 well Corning® tissue culture treated (TCT) microplates (10 K/2 mL/well). Cells were cultured at 37° C. for 1 day, 4 days, and 7 days before live/dead staining with Calcein AM and Ethidium homodimer-1 fluorescent dyes. The medium was changed at day 4. seeded on the surface of TCT controls. The cell attachment and growth of cells on composition 24 is better than the TCT control. The number of cells were counted using ImageJ software and are summarized as follows: 2A: 1 day=438; 4 day 418; and 7 day less than 100% confluent; 2B: 1 day=1549; 4 day 5252; and 7 day 100% confluent; and 2C: 1 day=463; 4 day 4561; and 7 day 100% confluent. When the cells are highly confluent on the surface of glass, the counting error increases. The images and cell counts are at least useful as qualitative measures and indicative of cell attachment and growth ability relative to the controls.

FIGS. 3A to 3C show time series optical images (low magnification of 2.5×) of MC3T3-E1 cells seeded on the surface of polished glass discs (12.5 mm in diameter×2.0 mm thickness) placed in wells of 24 well Corning® tissue culture treated (TCT) microplates (10 K/2 ml/well). Cells were cultured at 37° C. for 1 day, 4 days, and 7 days before live/dead staining with Calcein AM and Ethidium homodimer-1 fluorescent dyes. The medium was changed at day 4. Examples of glass compositions having fixed CaO at 30.0 mol % listed in Table 1 include: control composition C-29 (B/P=0)(FIG. 3A); composition 31 (B/P=0.15)(FIG. 3B); and composition 32 (B/P=0.30)(FIG. 3C). The addition of $B_2O_3$ into phosphate glasses improves biocompatibility. The number of cells were counted using ImageJ software and are summarized as follows: 3A: 1 day=33; 4 day 89; and 7 day less than 10; 3B: 1 day=975; 4 day 5673; and 7 day 100% confluent; and 3C: 1 day=898; 4 day 5538; and 7 day 100% confluent.

Figure 3:
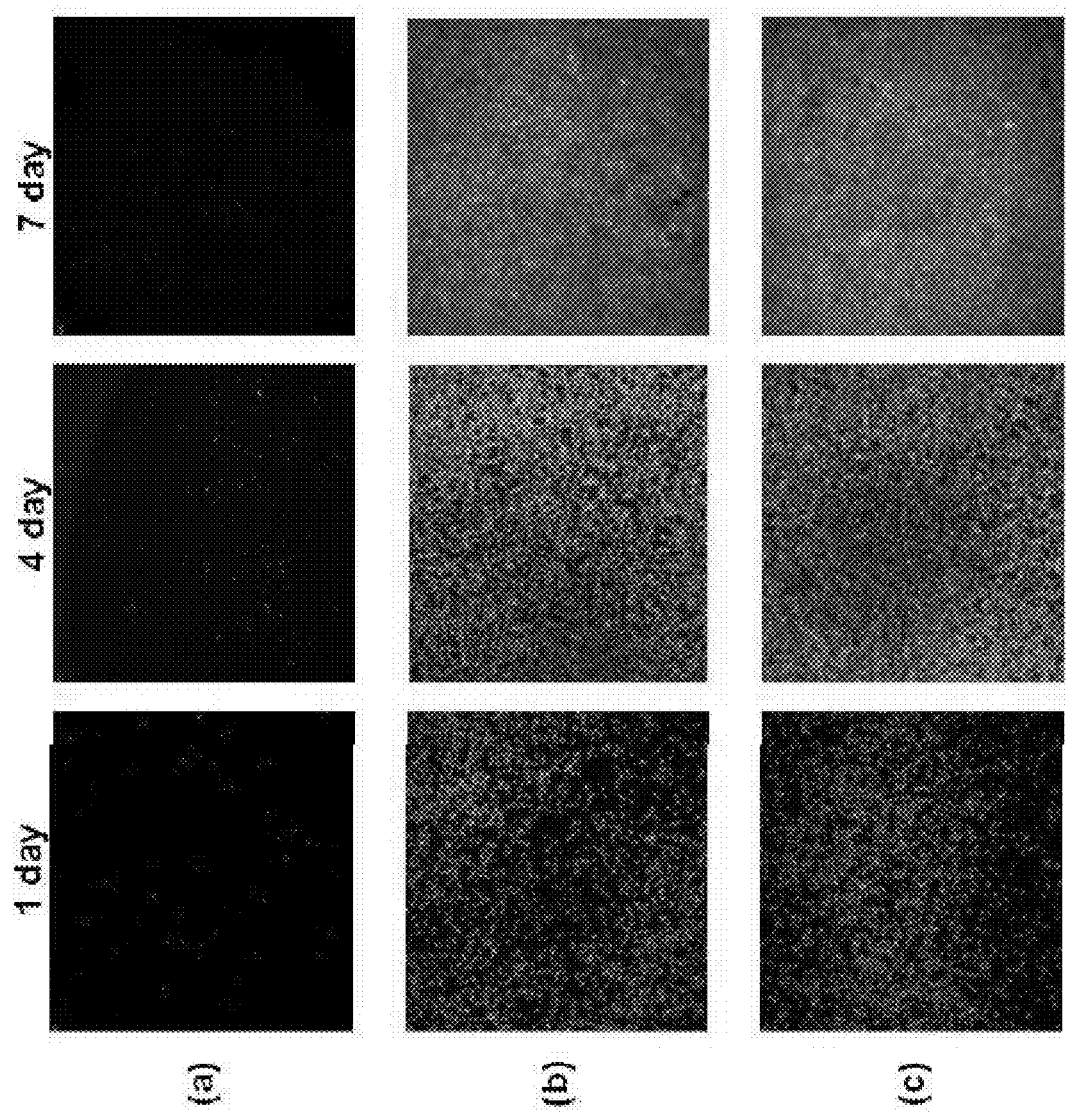
FIGS. 3A to 3C show time series optical images (low magnification of 2.5×) of MC3T3 cell seeded on the surface of selected polished glass discs.

Glass compositions in the phosphate-rich area with additives ZnO and MgO are listed in Table 1: Examples C-29, 30 to 33, C-34, 35 to 38, 40, and 42. The biocompatibility of these compositions was tested with MC3T3-E1 cells, and the angiogenesis ability was tested with HUVEC-2 cells (human umbilical vein endothelial cells). Glass compositions 30, 31, 32, 33 and control composition C-34, that had relatively low phosphorus content, exhibited good cell attachment and proliferation results (see examples in FIG. 3), but they also lead to cell death at day 4 under the circumstance of no medium change after cell seeding. FIGS. 3A to 3C also shows for glasses having fixed CaO at 30.0 mol %, a small addition of $B_2O_3$ improves the biocompatibility in this system. Cell growth and proliferation in the system, including $Na_2O$, $K_2O$, ZnO, and MgO additives is comparable to glasses with additives $Na_2O$ and $Al_2O_3$ but the compositions having one or more of the $K_2O$, ZnO, and MgO additives, led to more cell death after 4 days of culture.

Figure 4:
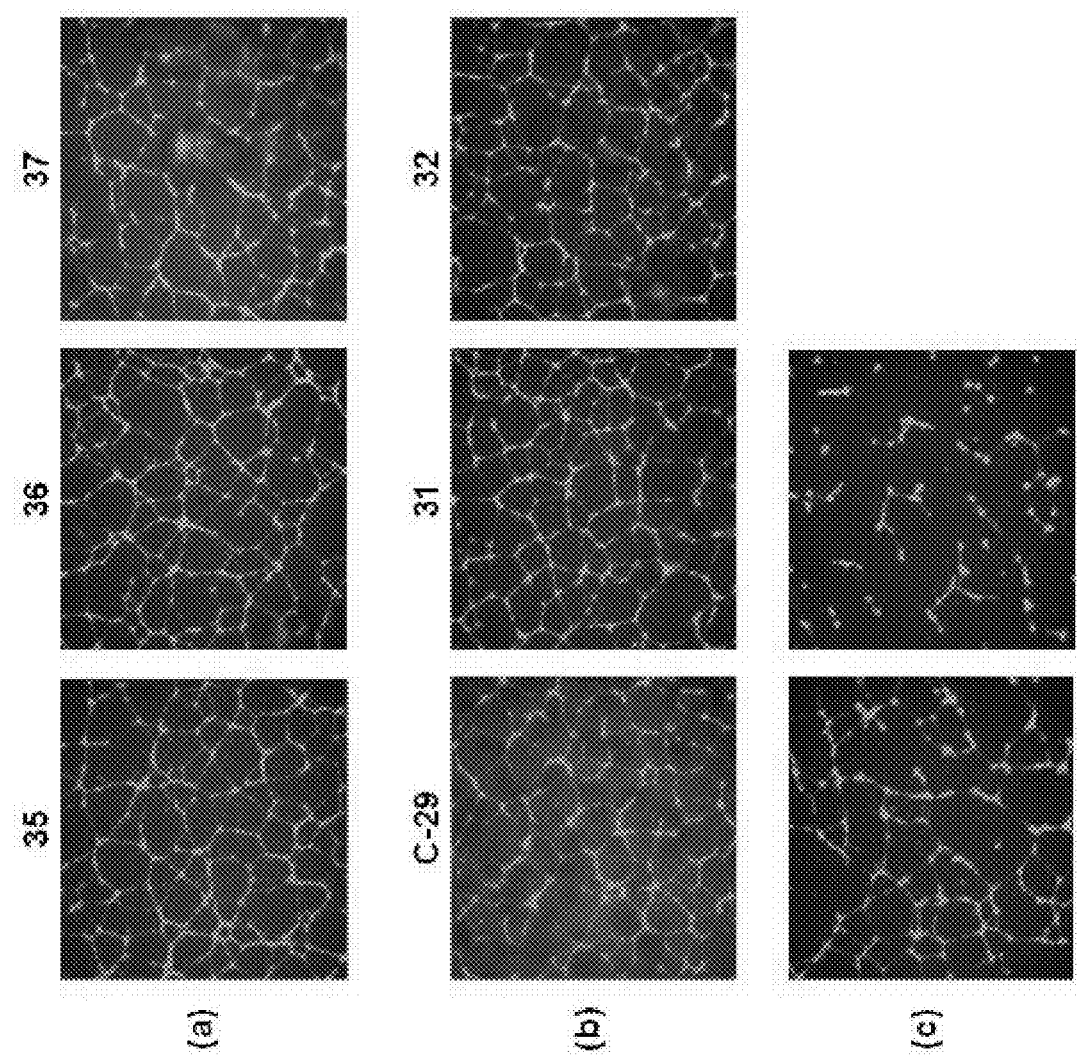
FIGS. 4A to 4C show optical images (low magnification of 2.5×) of an angiogenesis assay.

FIGS. 4A to 4C show optical images (low magnification of 2.5×) of an angiogenesis assay. Polished glass discs (12.5 mm in diameter×2.0 mm thickness) were placed into the bottom of separate wells, and Corning® Matrigel® was added on top of the glass surface and incubated at 37° C. for 30 min until gelation, then Corning® HUVEC-2 cells were seeded on the top of matrigel and cultured for 16 to 18 hrs. The tube formation was measured after labelling with Corning® AM fluorescent dye. HUVEC-2 culture medium: Lonza EBM™ Basal Medium with 2% Fetal Bovine Serum, ascorbic acid, hydrocortisone, and epidermal growth factor, vascular endothelial growth factor, insulin-like growth factor-1, human Fibroblast Growth Factor-Beta (hFGF-β), and Heparin. Examples of glass compositions in the CaO—$P_2O_5$—$B_2O_3$ system can include, for example: fixed $B_2O_3$ at about 1 mol % (FIG. 4A; Example 35 Ca/P=0.19, 93 loops; Example 36 Ca/P=0.12, 88 loops; Example 37 Ca/P=0.7, 73 loops); fixed CaO at about 30 mol % (FIG. 4B; control composition C-29 B/P=0, 121 loops; example 31 B/P=0.15, 95 loops; and example 32 B/P=0.3, 91 loops); and TCT control (43 loops)(left image) and gelatin coated glass control (0 loops)(right image)(FIG. 4C). The measured tube formation (measured in "loop" counts) shows that the disclosed inventive glasses have superior angiogenesis ability compared to the TCT control and the gelatin coated glass control. A change in glass composition also affects the angiogenesis ability. A greater Ca/P mol ratio results in a glass having superior angiogenesis ability compared to glasses with a lower Ca/P mol ratio, and the addition of $B_2O_3$ into the phosphate glasses decreases angiogenesis activity but is still superior to the gelatin coated glass and the TCT controls. Angiogenesis results showed that glass example control compositions C-29, C-34, and C-61, and the example compositions 1, 22, 23, 24, 25, 27, 30, 31, 32, 35, 36, 37, 46, and 47, had better angiogenesis ability than the control (see the examples in Table 4).

Figure 5:
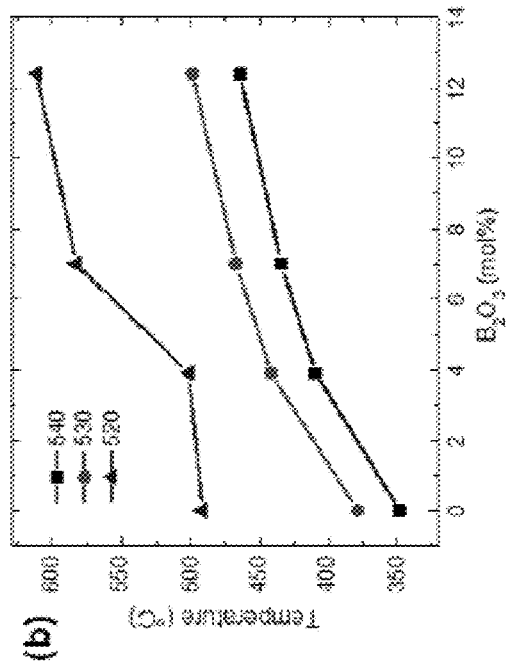
FIGS. 5A to 5C show graphs of properties that changed with a change in composition for selected example glasses having fixed CaO of about 30 mol %.
Figure 5:
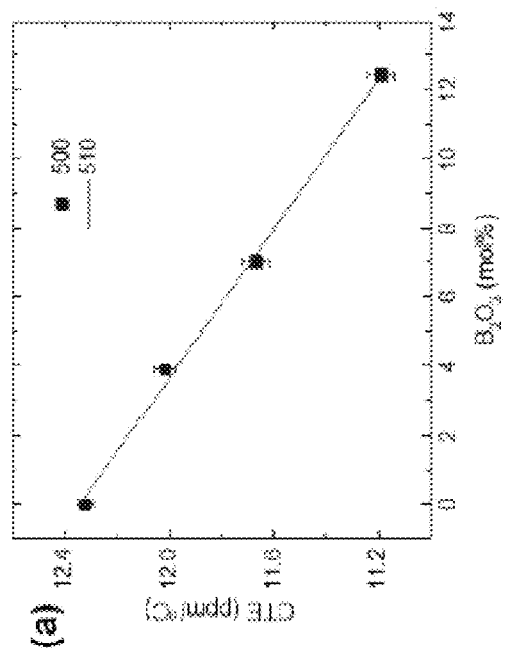
Figure 5:
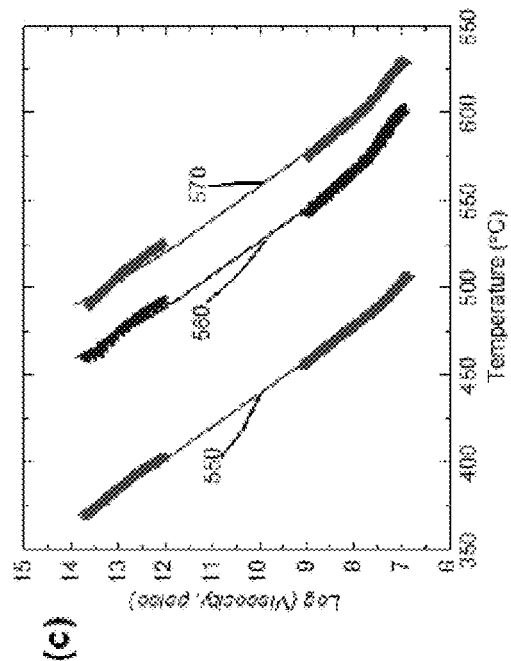

FIGS. 5A to 5C show graphs of properties that changed with a change in composition for the example glasses having fixed CaO of about 30 mol %: CTE (less than 300° C., on heating) (FIG. 5A: measured (500; squares); fitted line (510); $R^2$=0.995; slope=−0.093±0.004; intercept=12.34±0.03)); FIG. 5B: strain temperature (540), annealing temperature (530), and softening temperature (520); and FIG. 5C: a viscosity curve below 650° C. by beam bending viscosity (BBV), and parallel plate viscosity (PPV) for control example composition C-29 (550), example composition 31 (560), and example composition 32 (570). An increase in $B_2O_3$ content results in: a linear decrease in CTE (i.e., less than 300° C.); the strain, the annealing points, and the softening points all increase. Table 2 lists the glass physical properties and mechanical properties, e.g., stain temperature, annealing temperature, and softening temperature, CTE, Young's modulus, the shear modulus, and the Poisson's ratio for example glasses in CaO—$P_2O_5$—$B_2O_3$ system, including example glasses having an addition of $Li_2O$, $Al_2O_3$, and $TiO_2$ (e.g., compositions 10, 11, 13, 14, 15, 23, and 24, and control compositions C-63 and C-64) provide a greater Young's modulus and shear modulus).

Figure 6:
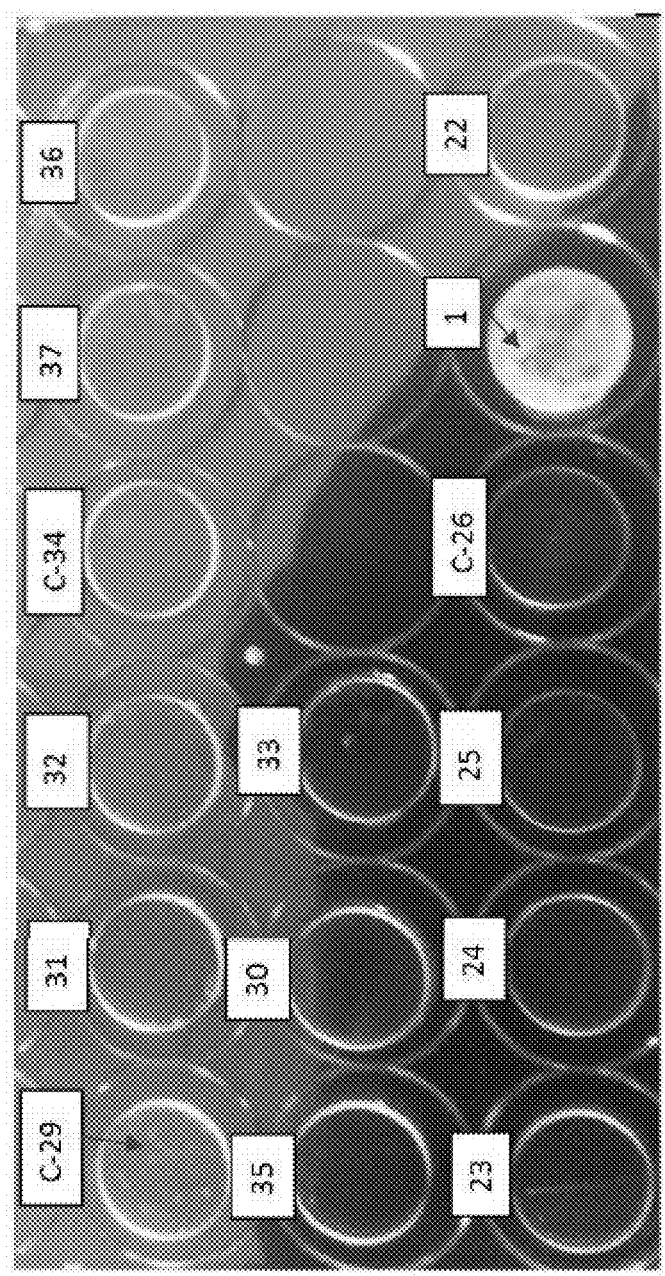
FIG. 6 shows surface morphology for selected glass compositions after a 7-day cell culture.

Dissolution rates or degradation rates of various ions from the glass can depend on the composition. The composition dissolution can further affect the glass biocompatibility. FIG. 6 shows glass surface morphology after 7 days cell culture with MC3T3-E1 cells. A glass surface of glass example control composition C-29 formed flake spots and the surface of composition 1 formed a layer of white flake (two samples indicated with an arrow). The cell culture medium color changed to yellow (pH less than 6.8) for glass example control composition C-29 and example composition 37, and the cell culture medium color changed to pink (pH greater than 8.2) for control glass composition 1. The cell culture results indicates without the addition of $Al_2O_3$ or $B_2O_3$, the relatively fast degradation rates of calcium borophosphate and calcium phosphate are unfavorable for cell attachment and proliferation. The various ions leached from the glass results in the different biocompatibility properties. For example, glass example control composition C-29 shows excellent angiogenesis ability but has poor cell attachment and poor proliferation performance (see FIGS. 3 and 4). This suggests that the glass composition can be tailored for desired product applications.

Figure 7:
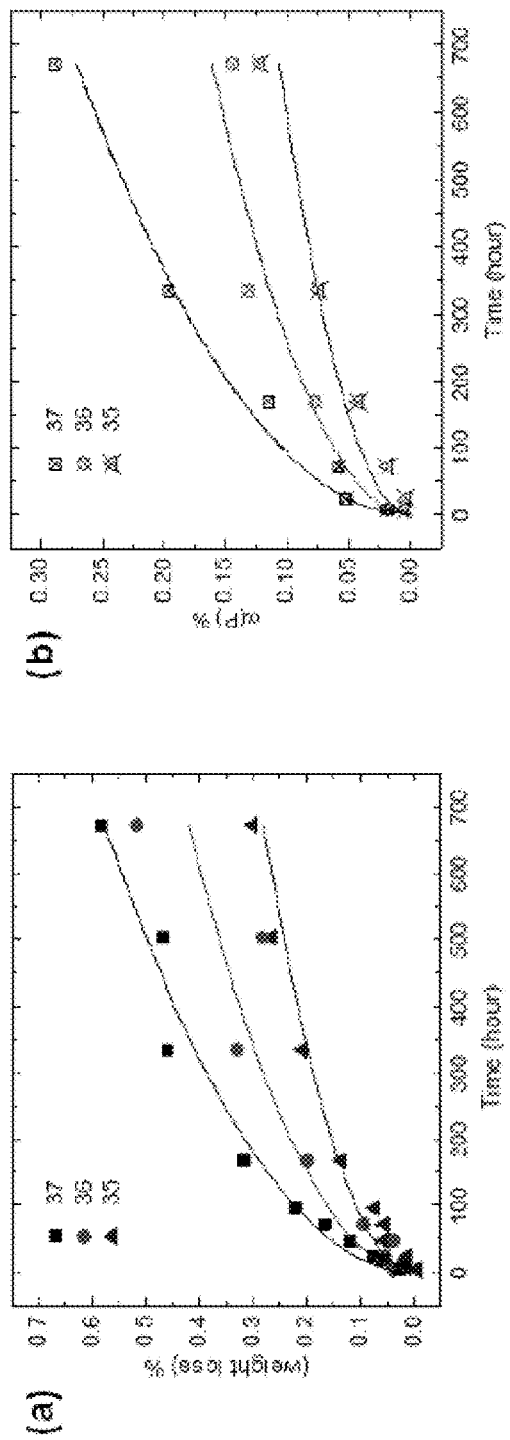
FIGS. 7A to 7D show the dissolution of selected example glass compositions in simulated body fluid (SBF) for 28 days.
Figure 7:
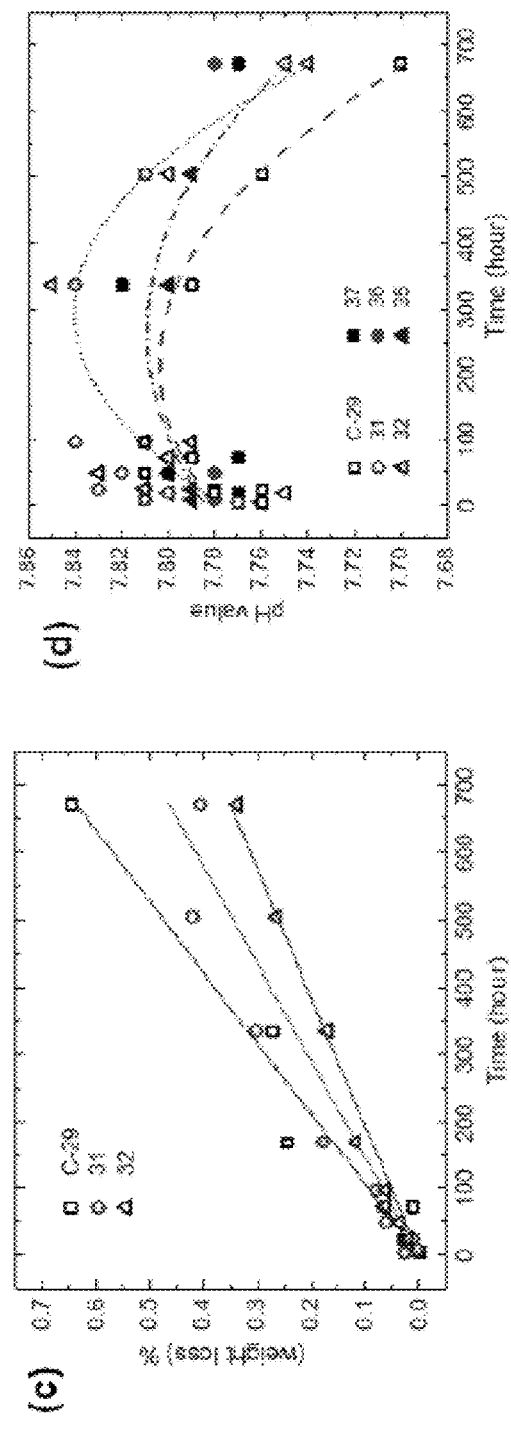

FIGS. 7A to 7D show the dissolution data for indicated example composition glasses in simulated body fluid (SBF) for 28 days: (weight loss) % ($=A \times t^{1/2}$) for glasses with fixed $B_2O_3$ at about 1 mol % (example 37 CaO=9.7 mol %; example composition 36 CaO=16.2 mol %; example composition 35 CaO=23.3 mol %), and data the was fitted by half-time dependence (FIG. 7A); $\alpha$(P) wt % ($=B \times t^{1/2}$) or the wt % phosphorous leached from the glasses into SBF solution was analyzed by ICP for glasses with fixed $B_2O_3$ at about 1 mol %, and the data was fitted by half-time dependence (FIG. 7B); (weight loss) % ($=C \times t$) for glasses with fixed CaO at about 30 mol %, and the data was fitted by linear time dependence (FIG. 7C: for example control composition C-29, and example compositions 31 and 32); changes in pH during the 28 days dissolution time, and dotted lines are guides (FIG. 7D: for example control composition C-29, and example compositions 31, 32, 35, 36, and 37). The constants A, B, and C, in the above equations are temperature-dependent dissolution rate parameters. Example compositions are listed in Table 1 and the reagents for an SBF solution are listed in Table 3.

Referring again to FIGS. 7A to 7D, for glasses having fixed $B_2O_3$ content (e.g., compositions 37, 36, and 35), an increase in CaO content or Ca/P mol ratio results in superior chemical durability, and the dissolution behavior shows half time dependence in SBF solution (FIG. 7A). The weight percentage of phosphorus species leached out from glass network into SBF solution also shows half-time dependence, and similarly, a greater CaO content or Ca/P ratio decreases the leaching rates of phosphorus (FIG. 7B). For glasses having a fixed CaO content (e.g., example control composition C-29, and example compositions 31 and 32), an increase in $B_2O_3$ content or B/P ratio results superior chemical durability, and the dissolution behavior shows a linear time dependence in SBF solution (FIG. 7C). The pH values of the SBF solutions during 28 days of dissolution time remain between from about 7.70 to about 7.86, then increase at the initial dissolution stage (i.e., less than 300 hrs), and then decrease during the later dissolution stage (i.e., from 300 to about 700 hrs)(FIG. 7D).

Figure 8A:
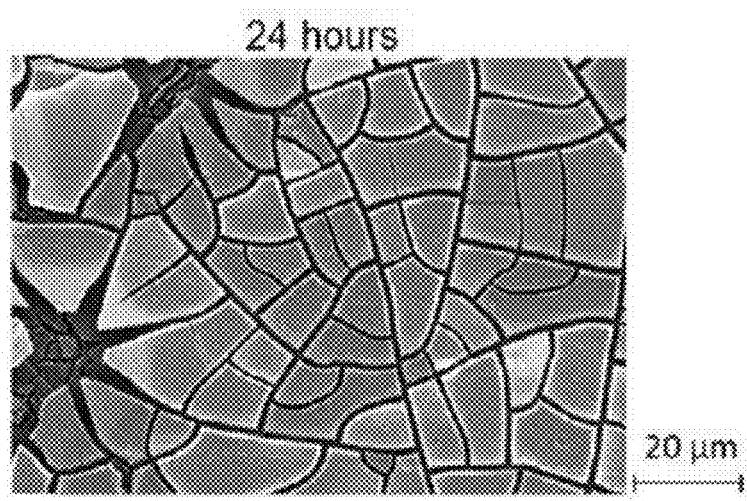
FIGS. 8a to 8p show SEM images of selected example glass compositions: surface (top image) and cross-section (bottom image) after soaking in SBF solution for 24 hrs, and soaking in SBF solution for 336 hrs.
Figure 8B:
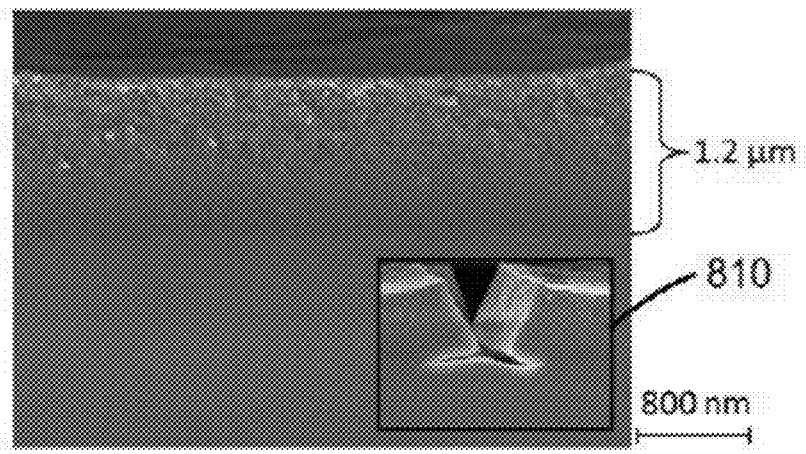
Figure 8C:
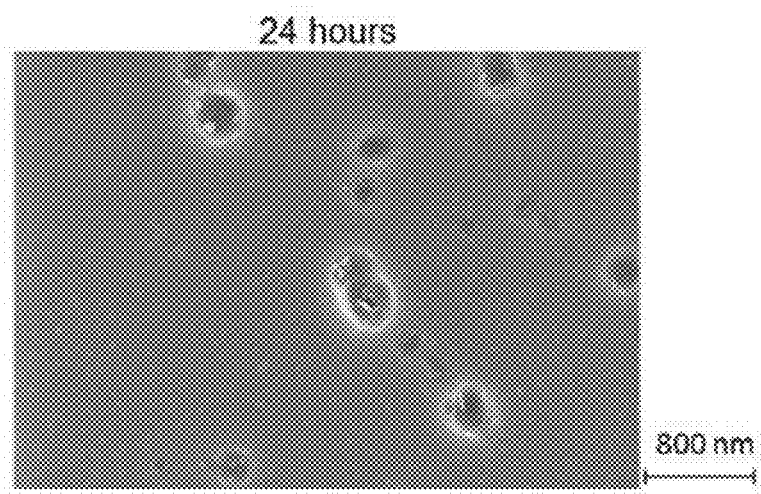
Figure 8D:
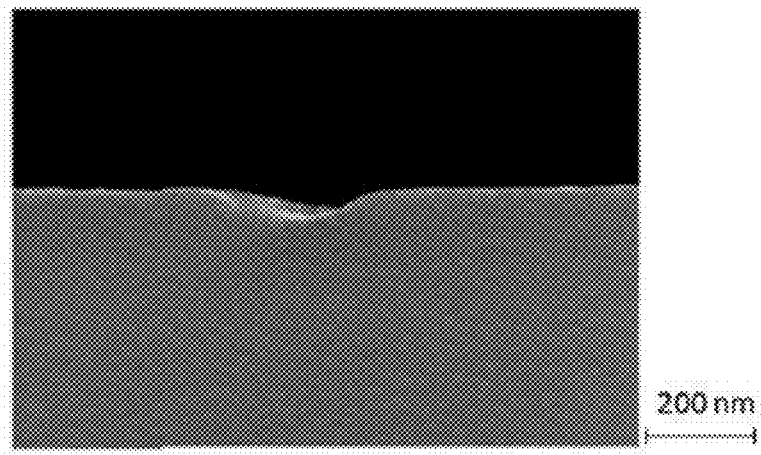
Figure 8E:
Figure 8F:
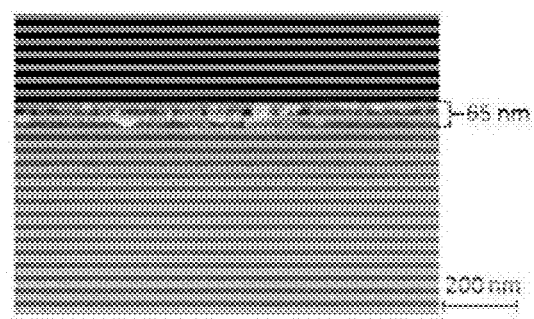
Figure 8G:
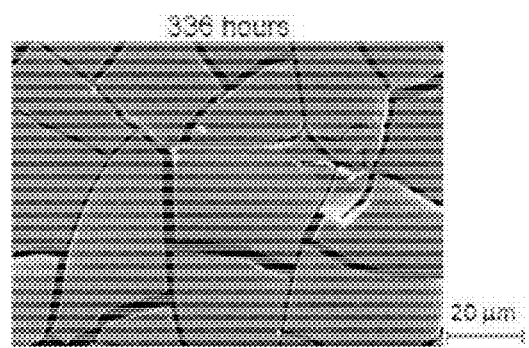
Figure 8H:
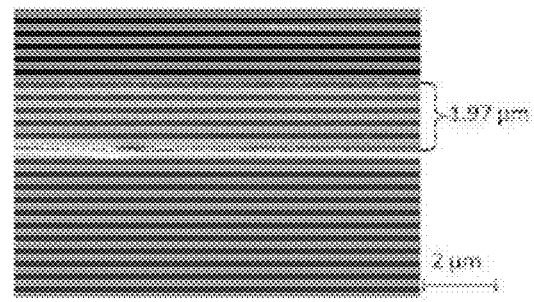
Figure 8I:
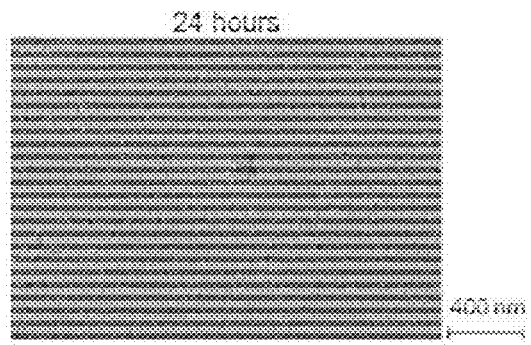
Figure 8J:
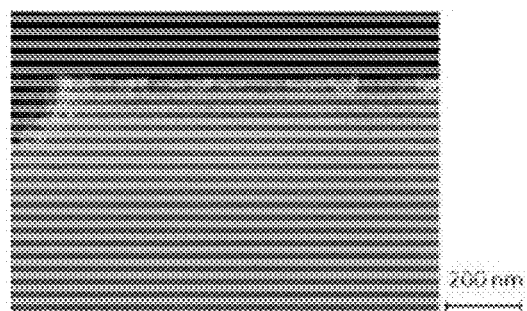
Figure 8K:
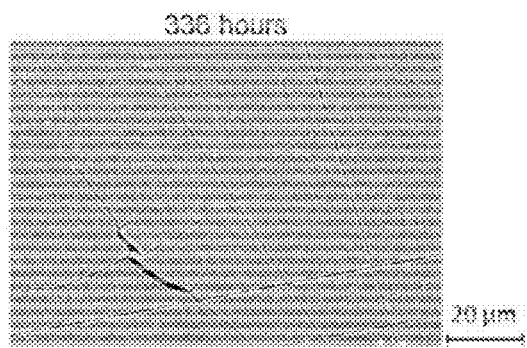
Figure 8L:
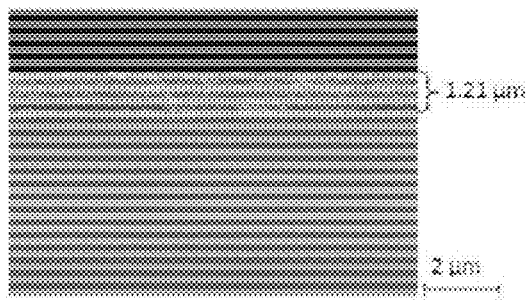
Figure 8M:
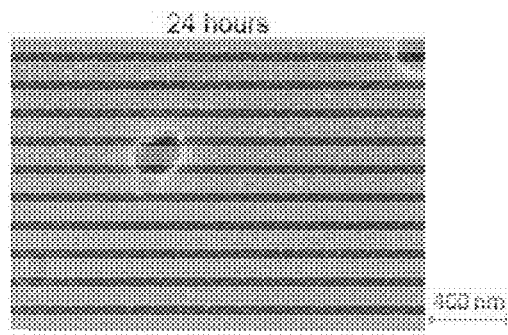
Figure 8N:
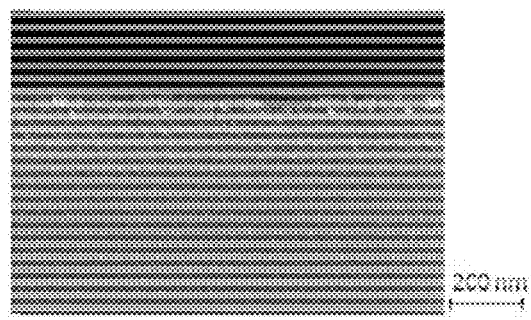
Figure 8O:
Figure 8P:
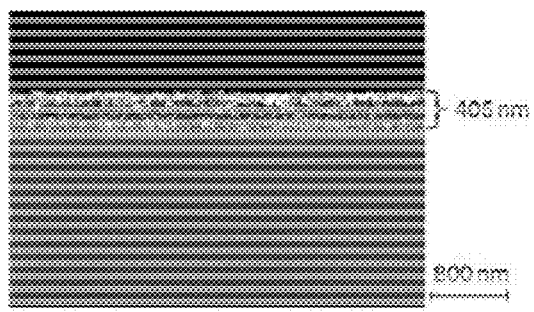

FIGS. 8a to 8p show SEM images of example glass surface (top image) and cross-section (bottom image) after soaking in SBF solution for 24 hrs for example control composition C-29 and example composition 32, and soaking in SBF solution for 24 hrs and 336 hrs for each of compositions 37, 36, and 35. Example control composition C-29 is shown in FIGS. 8a and 8b. Example composition 32 is shown in FIGS. 8c and 8d. Example composition 37 is shown in FIGS. 8e to 8h. Example composition 36 is shown in FIGS. 8i to 8l. Example composition 35 is shown in FIGS. 8m to 8p. Example control composition C-29 and example composition 32 have fixed CaO at about 30 mol %. Example compositions 37, 36, and 35, have fixed $B_2O_3$ at about 1 mol %. Alteration layers were formed and clearly observed for glasses with less chemical durability (e.g., control composition C-29 and composition 37). The glass surface morphology for short time dissolution (e.g., 24 hrs) also shows differences for glasses having fixed $B_2O_3$ and having fixed CaO content.

Glasses having fixed $B_2O_3$ content of about 1 mol % showed a half-time dependence on dissolution behavior in the SBF solution (FIG. 7a), where a visible porous structure was observed, especially for glasses having less chemical durability (e.g., composition 37; see also shown in FIGS. 8e to 8h FIG. 8c SEM image). Glasses having fixed CaO content of about 30 mol % showed a linear-time dependence on dissolution behavior in the SBF solution (FIG. 7c), where cracks were formed on the glass surface for glasses having less chemical durability (e.g., control composition C-29; see also inset crack (810) shown in FIG. 8b SEM image), and no visible porous structure was observed for example glasses having the fixed CaO content (FIGS. 8c and 8d). The x-ray analysis of the alteration layers detected an enrichment of sodium, magnesium, calcium, and oxygen, and a depletion of phosphorus, potassium, relative to the bulk glass after 2 and 4 weeks in SBF solutions. The dissolution study for selected disclosed glasses in CaO—$P_2O_5$—$B_2O_3$ system demonstrated the dependence of glass dissolution behavior on glass compositions in aqueous solution. The surface morphology during dissolution is strongly dependent on glass composition.

In embodiments, the glass properties depend on the glass composition and the glass structure. For a CaO—$B_2O_3$—$P_2O_5$ glass system having various additives, the $P_2O_5$ can serve as primary network former, which is expected to be present in a glass network as $Q^3$, $Q^2$, $Q^1$, and $Q^0$ tetrahedra (superscript indicates the number of bridging oxygens in one phosphate tetrahedra). For phosphate-rich compositions, the dissolution rate of phosphorus from the glass network controls the glass degradation rates. Fast degradation rates of the phosphate glasses could result in an acidic environment and cause cytotoxicity (e.g., composition 32). Fortunately, the disclosed phosphate glass compositions and their degradation rates can be easily tailored for desired end applications and their use requirements.

In embodiments, the $B_2O_3$ source can serve as the secondary network former, which is expected to be 3 and 4 coordinated sites in the glass network. The presence of the $B_2O_3$ affects glass forming ability, e.g., a small addition of $B_2O_3$ (e.g., about 4 mol %) improves the glass formability of calcium metaphosphate. The addition of the $B_2O_3$ into the phosphate glasses affects the glass properties, e.g., with an increase in the $B_2O_3$ content, the glass CTE (less than 300° C.) decreases; strain, annealing, and softening points increase; and viscosity difference between compositionally related samples increases at certain temperature, e.g., see FIG. 5C. The addition of $B_2O_3$ into the phosphate glass compositions also improves the cell attachment and proliferation performance of the phosphate-rich glasses (see, e.g., FIG. 3 and FIG. 4).

In embodiments, the $Al_2O_3$ content can also serve as a glass former in the disclosed example compositions. The addition of $Al_2O_3$ generally increases, for example, the glass forming ability, the viscosity of the melts, and the chemical durability of the compositions. The addition of a small amount of $Al_2O_3$ (e.g., about 5 mol %) is believed to be mainly 4-coordinated in the glass network, and the $Al_2O_3$ improves the cell growth properties as shown by cell attachment results (see FIG. 2 FIGS. 2A to 2C).

In embodiments, the alkali oxides (e.g., $Li_2O$, $Na_2O$, and $K_2O$) can serve as additives to modify, for example, the melting temperature, the viscosity, the mechanical strength, and the chemical durability of the compositions. The alkali oxides can also serve as a source of biologically active ions which can activate genes to synthesize growth factors and promote cell proliferation and differentiation (see for example, L. Hench, and J. Jones, eds., Biomaterials, artificial organs and tissue engineering. Elsevier, 2005).

Metal oxides (such as CaO, ZnO, MgO, $Fe_2O_3$/FeO, CuO/$Cu_2O$, and $TiO_2$) can also serve as additives to modify glass chemical durability, mechanical strength, and bioactivity. These additives were also found to promote cell adhesion/attachment and proliferation, and/or provide bacteriostatic and bactericidal effects (see E. A. Abou Neel, et al., "Effect of iron on the surface, degradation and ion release properties of phosphate-based glass fibres." *Acta Biomaterialia* 1, no. 5 (2005): 553-563; E. A. Abou Neel, et al., "Characterisation of antibacterial copper releasing degradable phosphate glass fibres." *Biomaterials* 26, no. 15 (2005): 2247-2254; and I. Ahmed, et al., "Processing, characterisation and biocompatibility of iron-phosphate glass fibres for tissue engineering." *Biomaterials* 25, no. 16 (2004): 3223-3232).

In embodiments, the disclosure provides methods of making the disclosed glass compositions that can be processed by various techniques into various forms, for example, a powder, a fiber, a bead, a sheet, a 3D scaffold, and like forms, or combinations thereof. Glass powder can be prepared by milling techniques; fiber can be made by spinning or drawing methods; beads can be produced by a flame forming method and flowing glass particles through a vertical furnace; sheets can be manufactured using thin rolling and/or floating processes; and scaffolds can be produced using, for example, rapid prototyping, polymer foam replication and particle sintering, and like methods. Glasses having desired properties and forms can be used to support cell growth and proliferation in cell culture, promote soft and hard tissue regeneration, stimulation of gene expression or angiogenesis (e.g., wound healing), deliver effective ions, deliver factors, or deliver both, for example, in cosmetics, health care, and like applications.

EXAMPLES

The following Examples demonstrate making, use, and analysis of the disclosed compositions and methods in accordance with the above general procedures.

Example 1

Preparation of Compositions 1 to 73

The respective source batch materials in the indicated amounts, including the indicated additives, as listed in Table 1, were individually weighted and mixed in a plastic jar using a Turbula® mixer. Next the batch mixture for each composition was transferred to a platinum crucible having an internal volume of approximately 1800 mL. The batch was calcined at 380° C. for 12 hrs before being melted in air in an electric furnace at from 1200° C. to 1500° C. for 4 hrs with an aluminum cover. The individual batch glass melts were poured into a steel mold (4 by 6 inch), and then annealed at from 350 to 550° C., depending on the composition.

Example 2

Procedure for Testing Biocompatibility and Angiogenesis

Selected example compositions in Table 4 were tested for biocompatibility and angiogenesis ability. The materials used for biocompatibility and angiogenesis ability were: MC3T3-E1 Subclone 14 (ATCC® CRL-2594™) from ATCC; 24 well tissue culture treated (TCT) microplates; human Umbilical Vein Endothelial Cells (HUVEC-2), Matrigel®, and Calcein AM fluorescent dye from Corning® Inc.; EBM™ Basal Medium and EGM™-2 SingleQuots™ Kit from Lonza; MEM alpha, nucleosides, no ascorbic acid (A1049001), One Shot™ Fetal Bovine Serum, sodium pyruvate, and gelatin-coated coverslip (neuVitro GG 15-gelatin) from Thermo Fisher Scientific.

Cell Attachment and Growth Procedure on Glass Discs.

Example glass discs (duplicates) having a diameter of 12.5 mm and a thickness 2.0 mm were individually placed into wells of tissue culture treated (TCT) microplates. For each microplate, two controls were included. One well included a gelatin-coated coverslip (gelatin control) and one well is without any glass discs or gelatin-coated coverslip (TCT control). MC3T3-E1 cells were seeded onto each example glass disc and each control with the cell amount of 10,000/2 mL/well. MC3T3-E1 culture medium is composed of MEM alpha containing 10% fetal bovine serum and 1 mM sodium pyruvate. Cells were cultured at 37° C. for 1 day, 4 days, and 7 days before live and dead staining using Calcein AM and Ethidium homodimer-1 fluorescent dyes. Medium was changed at day 4. The images were taken using a fluorescent microscope. The number of cells was counted using ImageJ software.

Angiogenesis Procedure.

Example glass discs (duplicates) having the above dimensions were individually placed into wells of TCT microplates. For each individual microplate, two controls were included as mentioned above. The TCT microplates were kept on ice (0° C.), and 400 microliters of Matrigel® was added to each well. Then the TCT microplates were incubated at 37° C. for 30 mins before HUVEC-2 cells were seeded on the top of matrigel in each well in the amount of $1.2 \times 10^5$/1 mL/well. HUVEC-2 culture medium is composed of Lonza EBM™ Basal Medium containing 2% fetal bovine serum, ascorbic acid, hydrocortisone, human epidermal growth factor (hEGF), vascular endothelial growth factor (VEGF), insulin-like growth factor-1 (IGF-1), human fibroblast growth factor-beta (hFGF-β), and heparin. The angiogenesis assay microplates were incubated at 37° C. for 16 to 18 hrs in 5% $CO_2$ atmosphere. The images were taken using a fluorescent microscope. The tube formation was measured by counting the number of loops after labeling with Corning® Calcein AM fluorescent dye.

The disclosure has been described with reference to various specific embodiments and techniques. However, it should be understood that many variations and modifications are possible while remaining within the scope of the disclosure.

What is claimed is:

1. A borophosphate glass composition consisting of:
   0.1 to 80 mol % $B_2O_3$,
   30 to 80 mol % $P_2O_5$, and
   5 to 50 mol % CaO, and
   at least two additives selected from:
   0.1 to 20 mol % $Li_2O$,
   0.1 to 20 mol % $Na_2O$,
   0.1 to 20 mol % $K_2O$,
   0.1 to 20 mol % $Al_2O_3$,
   0.1 to 10 mol % ZnO,
   0.1 to 3.6 mol % MgO,
   0.1 to 5 mol % $Fe_2O_3$,
   0.1 to 5 mol % CuO, and
   0.1 to 5 mol % $TiO_2$, based on a 100 mol % total of the composition.

2. The borophosphate glass composition of claim 1, wherein any additive selected from the group of $Al_2O_3$, ZnO, MgO, $Fe_2O_3$, and CuO retards the degradation rate of glass formers $B_2O_3$, $P_2O_5$, or both, going from a solid state into a solution state.

3. The borophosphate glass composition of claim 1, wherein any additive selected from the group of LiO, $Na_2O$, and $K_2O$ increases the degradation rate of the glass composition going from a solid state into a solution state.

4. A bioactive composition, comprising
   (a) a borophosphate glass composition consisting of:
   0.1 to 80 mol % $B_2O_3$,
   30 to 80 mol % $F_2O_5$, and
   5 to 50 mol % CaO, and
   at least two additives selected from;
   0.1 to 20 mol % $Li_2O$,
   0.1 to 20 mol % $Na_2O$,
   0.1 to 20 mol % $K_2O$,
   0.1 to 20 mol % $Al_2O_3$,
   0.1 to 10 mol % ZnO,
   0.1 to 3.6 mol % MgO,
   0.1 to 5 mol % $Fe_2O_3$,
   0.1 to 5 mol % CuO, and
   0.1 to 5 mol % $TiO_2$, based on a 100 mol % total of the borophosphate glass composition; and
   (b) a least one live cell.

5. The bioactive composition of claim 4, wherein the at least one live cell is selected from the group consisting of MC3T3-E1 cells, human umbilical vein endothelial cells, or combinations thereof.

6. The bioactive composition of claim 4, wherein one of the at least two additives is 0.1 to 6 mol % $Al_2O_3$, and the bioactive composition has an improved biocompatibility compared to the same bioactive composition free of $Al_2O_3$.

7. An article of manufacture comprising the borophosphate glass composition of claim 1.

8. The article of manufacture of claim 7, further comprising: at least one form factor selected from: a cell culture article or apparatus; a cell phone cover glass component; a flat or curved panel display component; a structural glass component; a pharmaceutical drug dispensing vial component; a fiber optic component, or a combination thereof.

9. A method of inhibiting the release of at least one of $B_2O_3$ and $P_2O_5$ present in the borophosphate glass composition of claim 1 into an aqueous solution, wherein the borophosphate glass composition has at least one additive selected from the group consisting of $Al_2O_3$, ZnO, MgO, $Fe_2O_3$, and CuO, the method comprising:
   contacting the borophosphate glass composition with an aqueous solution.

10. The method of claim 9, wherein the aqueous solution is a simulated body fluid, and where the measured inhibition is relative to, or compared with, the same borophosphate glass composition but free of the at least one additive source selected from the group of $Al_2O_3$, ZnO, MgO, $Fe_2O_3$, and CuO.

11. A method of increasing the release of at least one of $B_2O_3$ and $P_2O_5$ present in the borophosphate glass composition of claim 1 into an aqueous solution, wherein the borophosphate glass composition of claim 1 has at least one additive selected from the group consisting of LiO, $Na_2O$, $K_2O$, and $SiO_2$, the method comprising:
    contacting the borophosphate glass composition with a liquid.

12. The method of claim 11, wherein the liquid is water, an aqueous solution, a simulated body fluid, or mixtures thereof.

13. The method of claim 11, wherein the contacting is conducted in the presence of at least one entity selected from a cell; a tissue; an organ; a blood vessel, or a combination thereof, and wherein the contacting enhances the bioactivity interaction properties of the composition and the at least one entity for at least one of biocompatibility; angiogenesis; or both biocompatibility and angiogenesis.

14. A method of proliferating cells on a bioactive glass composition in an aqueous solution comprising:
    contacting the bioactive glass composition claim 4 in the aqueous solution for a time sufficient to proliferate the at least one live cell.

15. The method of claim 14, wherein the aqueous solution is a simulated body fluid, and the at least one live cell is a live entity selected from selected from: a cell; a tissue; an organ; a blood vessel, or a combination thereof.

16. The borophosphaLe glass composition of claim 1, wherein the composition consists of:
    0.1 to 80 mol % $B_2O_3$,
    30 to 80 mol % $P_2O_5$, and
    5 to 50 mol % CaO, and
    at least two additives selected from:
    0.1 to 20 mol % $Li_2O$,
    0.1 to 20 mol % $Na_2O$,
    0.1 to 20 mol %% $K_2O$,
    5 to 20 mol % $Al_2O_3$,
    0.1 to 10 mol % ZnO,
    0.1 to 5 mol % $Fe_2O_3$,
    0.1 to 5 mol % CuO, and
    0.1 to 5 mol % $TiO_2$, based on a 100 mol % total of the composition.

17. The borophosphate glass composition of claim 1, wherein the composition consists of:
    0.1 to 80 mol % $B_2O_3$,
    30 to 80 mol % $P_2O_5$, and
    5 to 50 mol % CaO, and
    at least two additives selected from:
    0.1 to 20 mol % $Li_2O$,
    0.1 to 20 mol % $Na_2O$,
    5 to 20 mol % $Al_2O_3$,
    0.1 to 5 mol % $Fe_2O_3$,
    0.1 to 5 mol % CuO, and
    0.1 to 5 mol % $TiO_2$, based on a 100 mol % total of the composition.

18. The borophosphate glass composition of claim 1, wherein the composition consists of:
    0.1 to 80 mol % $B_2O_3$,
    30 to 80 mol % $P_2O_5$,
    5 to 50 mol % CaO,
    0.1 to 20 mol % $Na_2O$,
    5 to 20 mol % $Al_2O_3$, based on a 100 mol % total of the composition.

19. The borophosphate glass composition of claim 1, wherein the composition consists of:
    4 to 80 mol % $B_2O_3$,
    30 to 80 mol % $P_2O_5$,
    5 to 50 mol % CaO,
    0.1 to 20 mol % $Na_2O$,
    5 to 20 mol % $Al_2O_3$, based on a 100 mol % total of the composition.

* * * * *

UNITED STATES PATENT AND TRADEMARK OFFICE
CERTIFICATE OF CORRECTION

Page 1 of 2

PATENT NO. : 10,676,713 B2
APPLICATION NO. : 15/602899
DATED : June 9, 2020
INVENTOR(S) : Huayun Deng et al.

It is certified that error appears in the above-identified patent and that said Letters Patent is hereby corrected as shown below:

On the Title Page

In Column 2, Item (57), Abstract, Line 10, delete "aborophosphate" and insert -- a borophosphate --, therefor.

On page 2, in Column 2, Item (56), Other Publications, Line 27, delete "baed" and insert -- based --, therefor.

On page 2, in Column 2, Item (56), Other Publications, Line 28, delete "Sciemce" and insert -- Science --, therefor.

On page 3, in Column 1, Item (56), Other Publications, Line 44, delete "Manetization" and insert -- Magnetization --, therefor.

On page 3, in Column 1, Item (56), Other Publications, Line 55, delete "Prepareation" and insert -- Preparation --, therefor.

On page 3, in Column 1, Item (56), Other Publications, Line 59, delete "EMPRESST2" and insert -- EMPRESS 2 --, therefor.

On page 3, in Column 1, Item (56), Other Publications, Line 59, delete "EMPRESST" and insert -- EMPRESS --, therefor.

On page 3, in Column 1, Item (56), Other Publications, Line 64, delete "La;" and insert -- al; --, therefor.

On page 3, in Column 2, Item (56), Other Publications, Line 10, delete "Microplasitcs" and insert -- Microplastics --, therefor.

Signed and Sealed this
Eleventh Day of October, 2022

Katherine Kelly Vidal
*Director of the United States Patent and Trademark Office*

CERTIFICATE OF CORRECTION (continued)
U.S. Pat. No. 10,676,713 B2

On page 3, in Column 2, Item (56), Other Publications, Line 47, delete "Propmotes" and insert -- Promotes --, therefor On page 3, in Column 2, Item (56), Other Publications, Lines 58-59, delete "Si02-Na20-Fe203-Ca0-P205_B203" and insert -- SiO2-Na2O-Fe2O3-CaO-P2O5_B2O3 --, therefor.

In the Claims

In Column 22, Line 30, Claim 4, delete "$F_2O_5$" and insert -- $P_2O_5$ --, therefor.

In Column 22, Line 32, Claim 4, delete "from;" and insert -- from: --, therefor.

In Column 22, Line 43, Claim 4, delete "a least" and insert -- at least --, therefor.

In Column 23, Line 33, Claim 15, after "live entity", delete "selected from".

In Column 23, Line 35, Claim 16, delete "borophosphaLe" and insert -- borophosphate --, therefor.

In Column 24, Line 4, Claim 16, after "mol", delete -- % --.